(12) United States Patent
Sheldrake et al.

(10) Patent No.: US 8,592,581 B2
(45) Date of Patent: Nov. 26, 2013

(54) TRISUBSTITUTED PURINE DERIVATIVES

(75) Inventors: Peter William Sheldrake, Kent (GB); Butrus Atrash, Hants (GB); Simon Green, Dundee (GB); Edward McDonald, Reigate Surrey (GB); Sheelagh Frame, Perthshire (GB)

(73) Assignees: Cyclacel Limited, London (GB); Cancer Research Technology Limited, London (GB)

( * ) Notice: Subject to any disclaimer, the term of this patent is extended or adjusted under 35 U.S.C. 154(b) by 955 days.

(21) Appl. No.: 12/573,337

(22) Filed: Oct. 5, 2009

(65) Prior Publication Data

US 2010/0093769 A1 Apr. 15, 2010

Related U.S. Application Data

(63) Continuation of application No. PCT/GB2008/001173, filed on Apr. 2, 2008.

(60) Provisional application No. 60/921,897, filed on Apr. 4, 2007.

(51) Int. Cl.
*A61K 31/52* (2006.01)
*C07D 473/16* (2006.01)

(52) U.S. Cl.
USPC .................. 544/277; 514/263.22; 514/263.4

(58) Field of Classification Search
USPC ............................. 544/277; 514/263.22, 263.4
See application file for complete search history.

(56) References Cited

U.S. PATENT DOCUMENTS

| 6,627,633 | B2 * | 9/2003 | Trova | 514/263.2 |
| 6,790,958 | B2 * | 9/2004 | Lum et al. | 544/277 |
| 6,812,232 | B2 * | 11/2004 | Trova | 514/263.2 |
| 6,949,559 | B2 * | 9/2005 | Trova | 514/263.2 |
| 2003/0229105 | A1 * | 12/2003 | Kashanchi | 514/263.2 |
| 2004/0236084 | A1 * | 11/2004 | Biwersi et al. | 534/766 |
| 2008/0125404 | A1 * | 5/2008 | Benigni et al. | 514/171 |
| 2010/0143350 | A1 * | 6/2010 | Green et al. | 424/133.1 |

FOREIGN PATENT DOCUMENTS

| WO | 00/44750 A1 | 8/2000 |
| WO | WO-03/002565 A1 | 1/2003 |
| WO | WO-2004/016612 A2 | 2/2004 |
| WO | WO-2004/016613 A2 | 2/2004 |
| WO | WO 2006021803 A2 * | 3/2006 |

OTHER PUBLICATIONS

De Azevedo, Walter Filgueira et al., "Inhibition of cyclin-dependent kinases by purine analogues. Crystal structure of human cdk2 complexed with roscovitine," Eur. J. Biochem., vol. 243:518-526 (1997).
Haesslein, Jean-luc et al., "Recent Advances in Cyclin-Dependent Kinase Inhibition. Purine-Based Derivatives as Anti-Cancer Agents. Roles and Perspectives for the Future," Current Topics in Medicinal Chemistry, vol. 2:1037-1050 (2002).
International Preliminary Report on Patentability for Application No. PCT/GB2008/001173, dated Oct. 6, 2009.
Knockaert, Marie et al., "Pharmacological inhibitors of cyclin-dependent kinases," Trends in Pharmacological Sciences, vol. 23(9):417-425 (2002).
O'Hare, Michael et al., "Cyclin-dependent kinases as potential targets to improve stroke outcome," Pharmacology & Therapeutics, vol. 93:135-143 (2002).

* cited by examiner

*Primary Examiner* — Kortney L Klinkel
*Assistant Examiner* — John Mauro
(74) *Attorney, Agent, or Firm* — Nelson Mullins Riley & Scarborough LLP; Cynthia L. Kanik

(57) ABSTRACT

The present invention relates to compounds of formula (I)

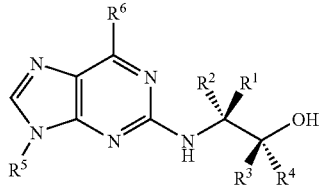

(I)

wherein:
$R^1$ and $R^2$ are each independently H, alkyl or haloalkyl;
$R^3$ and $R^4$ are each independently H, alkyl, haloalkyl or aryl;
$R^5$ is alkyl or cycloalkyl or cycloalkyl-alkyl, each of which may be optionally substituted with one or more OH groups;
$R^6$ is selected from cyclopropylamino, cyclopropylmethylamino, cyclobutylamino, cyclobutylmethylamino and

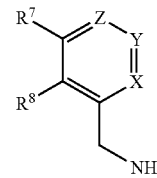

where one of X, Y and Z is N and the remainder are $CR^9$;
$R^7$, $R^8$ and each $R^9$ are independently H, alkyl or haloalkyl, wherein at least one of $R^7$,
$R^8$ and each $R^9$ is other than H.

A further aspect of the invention relates to pharmaceutical compositions comprising compounds of formula (I), and the use of said compounds in treating proliferative disorders, viral disorders, stroke, alopecia, CNS disorders, neurodegenerative disorders, or diabetes.

32 Claims, 1 Drawing Sheet

TRISUBSTITUTED PURINE DERIVATIVES

RELATED APPLICATIONS

This application is a continuation of PCT/GB2008/001173, which was filed on Apr. 2, 2008 and which claims priority to GB 0706632.7, which was filed on Apr. 4, 2007, and to U.S. 60/921,897, which was filed on Apr. 4, 2007. The entire contents of each of these applications are hereby incorporated herein by reference.

FIELD OF INVENTION

The present invention relates to new 2,6,9-substituted purine derivatives and their biological applications. In particular, the invention relates to purine derivatives having antiproliferative properties which are useful in the treatment of proliferative disorders such as cancer, leukemia, psoriasis and the like.

BACKGROUND

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1), cyclin D1-D3 (CDK2, CDK4, CDK5, CDK6), cyclin E (CDK2). Each of these complexes is involved in a particular phase of the cell cycle. Not all members of the CDK family are involved exclusively in cell cycle control, however. For example, CDKs 7, 8, and 9 are implicated in the regulation of transcription, whereas CDK5 plays a role in neuronal and secretory cell function.

The activity of CDKs is regulated post-translationally by transitory associations with other proteins and by alterations of their intracellular localisation. Tumour development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g. cyclin A/CDK2 and that it may be possible to develop novel antineoplastic agents devoid of the general host toxicity observed with conventional cytotoxic and cytostatic drugs. While inhibition of cell cycle-related CDKs is clearly relevant in e.g. oncology applications, this may not be the case for the inhibition of RNA polymerase-regulating CDKs. On the other hand, inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

WO 98/05335 (CV Therapeutics Inc) discloses 2,6,9-trisubstituted purine derivatives that are selective inhibitors of cell cycle kinases. Such compounds are useful in the treatment of autoimmune disorders, e.g. rheumatoid arthritis, lupus, type I diabetes, multiple sclerosis; treating cancer, cardiovascular disease, such as restenosis, host v graft disease, gout, polycystic kidney disease and other proliferative diseases whose pathogenesis involves abnormal cell proliferation.

WO 99/07705 (The Regents of the University of California) discloses purine analogues that inhibit inter alia protein kinases, G-proteins and polymerases. More specifically, the invention relates to methods of using such purine analogues to treat cellular proliferative disorders and neurodegenerative diseases.

WO 97/20842 (CNRS) also discloses purine derivatives displaying antiproliferative properties which are useful in treating cancer, psoriasis, and neurodegenerative disorders. Further purine derivatives are described in WO 03/002565, WO 04/016613 and WO 04/016612.

The present invention seeks to provide new 2,6,9-substituted purine derivatives, particularly those having antiproliferative properties.

STATEMENT OF INVENTION

A first aspect of the invention relates to a compound of formula I, or a pharmaceutically acceptable salt thereof,

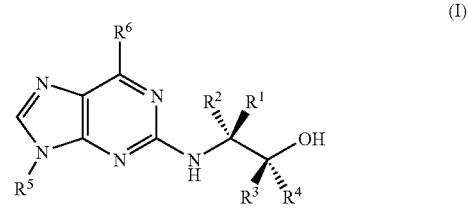

(I)

wherein:

$R^1$ and $R^2$ are each independently H, alkyl or haloalkyl;

$R^3$ and $R^4$ are each independently H, alkyl, haloalkyl or aryl;

$R^5$ is alkyl or cycloalkyl or cycloalkyl-alkyl, each of which may be optionally substituted with one or more OH groups;

$R^6$ is selected from cyclopropylamino, cyclopropylmethylamino, cyclobutylamino, cyclobutylmethylamino and

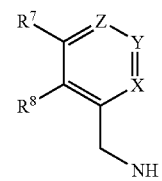

where one of X, Y and Z is N and the remainder are $CR^9$;

$R^7$, $R^8$ and each $R^9$ are independently H, alkyl or haloalkyl, wherein at least one of $R^7$, $R^8$ and each $R^9$ is other than H.

A second aspect of the invention relates to a compound of formula II, or a pharmaceutically acceptable salt thereof,

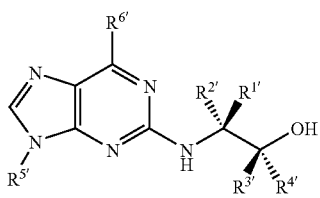

(II)

wherein:
at least one of $R^{1'}$, $R^{2'}$, $R^{3'}$ and $R^{4'}$ is haloalkyl and the remainder are each independently H, alkyl or haloalkyl;
$R^{5'}$ is alkyl or cycloalkyl or cycloalkyl-alkyl, each of which may be optionally substituted with one or more OH groups;
$R^{6'}$ is selected from cyclopropylamino, cyclopropylmethylamino, cyclobutylamino, cyclobutylmethylamino and

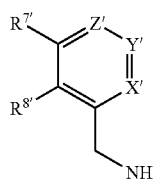

where X', Y' and Z' are each independently $CR^{9'}$, or one of X', Y' and Z' is N and the remainder are $CR^{9'}$; and
$R^{7'}$, $R^{8'}$ and each $R^{9'}$ are independently H, halo, alkyl or haloalkyl.

A third aspect of the invention relates to a pharmaceutical composition comprising a compound of the invention and a pharmaceutically acceptable carrier, diluent or excipient.

A fourth aspect of the invention relates to the use of a compound of the invention in the preparation of a medicament for treating one or more of the following disorders:
a proliferative disorder;
a viral disorder;
a stroke;
alopecia;
a CNS disorder;
a neurodegenerative disorder; and
diabetes.

A fifth aspect of the invention relates to the use of a compound of the invention as an anti-mitotic agent.

A sixth aspect of the invention relates to the use of a compound of the invention for inhibiting a protein kinase.

A seventh aspect of the invention relates to a method of treating a proliferative disease, said method comprising administering to a mammal a therapeutically effective amount of a compound of the invention.

An eighth aspect of the invention relates to the use of a compound of the invention in an assay for identifying further candidate compounds that influence the activity of one or more CDK enzymes.

DETAILED DESCRIPTION

As mentioned above, a first aspect of the invention relates to a compound of formula (I) as defined hereinabove.

As used herein, the term "alkyl" includes both saturated straight chain and branched alkyl groups. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl.

As used herein, the term "cycloalkyl" refers to a cyclic alkyl group. Preferably, the cycloalkyl group is a $C_{3-12}$ cycloalkyl group.

As used herein, the term "cycloalkyl-alkyl" refers to a group having both cycloalkyl and alkyl functionalities.

Preferably, one of $R^1$ and $R^2$ is H and the other is alkyl.
More preferably, one of $R^1$ and $R^2$ is H and the other is methyl, ethyl or isopropyl.

In one preferred embodiment, $R^1$ is ethyl and $R^2$ is H.

In one preferred embodiment of the invention, $R^3$ and $R^4$ are each independently H, alkyl, haloalkyl or aryl, and at least one of $R^3$ and $R^4$ is other than H.

In one preferred embodiment of the invention, one of $R^3$ and $R^4$ is H and the other is alkyl or haloalkyl.

In a more preferred embodiment, $R^3$ is H and $R^4$ is alkyl or haloalkyl.

More preferably, $R^3$ is H and $R^4$ is methyl.

In one preferred embodiment of the invention, $R^6$ is

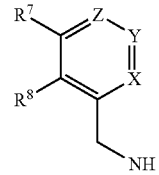

In one preferred embodiment of the invention, Y is N. 11. Preferably for this embodiment, X is CH, Z is C-alkyl, $R^7$ is H and $R^8$ is alkyl. More preferably, for this embodiment, X is CH, Z is C-Me and $R^7$ is H and $R^8$ is Me. In an alternative preferred embodiment, X is CH, Z is C-Me and $R^7$ and $R^8$ are both H. In yet another alternative preferred embodiment, X is CH, Z is C—$CF_3$ and $R^7$ and $R^8$ are both H.

In one preferred embodiment of the invention, X is N. Preferably, for this embodiment, Y is C-Me, Z is CH and $R^7$ and $R^8$ are both H. In yet another alternative preferred embodiment, Y and Z are CH, $R^7$ is H and $R^8$ is Me.

In one preferred embodiment of the invention, Z is N. Preferably, for this embodiment, X is CH, Y is C-Me, $R^7$ is Me and $R^8$ is H.

In another preferred embodiment of the invention, $R^6$ is cyclopropylamino, cyclopropylmethylamino, cyclobutylamino or cyclobutylmethylamino.

In another preferred embodiment of the invention, $R^5$ is isopropyl.

In one highly preferred embodiment, the compound of the invention is selected from the following:

[1] (2R,3S-3-(6-((4,6-Dimethylpyridin-3-ylmethylamino)-9-isopropyl-9H-purin-2-ylamino)pentan-2-ol
[2] 2R,3S-3-(9-isopropyl-6-((6-methylpyridin-3-yl)methylamino)-9H-purin-2-ylamino)pentan-2-ol
[6] 2R,3S-3-(6-Cyclopropylamino)-9-isopropyl-9H-purin-2-ylamino)pentan-2-ol
[7] 2R,3S-3-(6-(Cyclopropylmethylamino)-9-isopropyl-9H-purine-2-ylamino)pentan-2-ol
[8] 2R,3S-3-(6-(Cyclobutylamino)-9-isopropyl-9H-purin-2-ylamino)pentan-2-ol
[10] 2R,3S-3-(9-Isopropyl-6-(2,6-dimethylpyridine-4-ylmethylamino)-9H-purin-2-ylamino)pentan-2-ol
[11] 2R,3S-3-(9-Isopropyl-6-((6-(trifluoromethyl)pyridine-3-yl)methylamino)-9H-purin-2ylamino)pentan-2-ol -continued

[12] 2R,3S-3-(9-Isopropyl-6-((6-methylpyridin-2-yl)methylamino)-9H-purin-2-ylamino)pentan-2-ol
[13] 2R,3S-3-(9-Isopropyl-6-((3-methylpyridin-2-yl)methylamino)-9H-purin-2-ylamino)pentan-2-ol
[15] 1,1,1-Trifluoro-3-(9-isopropyl-6-(pyridin-3-ylmethylamino)-9H-purin-2-ylamino)propan-2-ol
[16] 1,1,1-Trifluoro-3-(9-isopropyl-6-(pyridin-3-ylmethylamino)-9H-purin-2-ylamino)pentan-2-ol
[17] 1,1,1-Trifluoro-3-(9-isopropyl-6-((6-(trifluoromethyl)pyridin-3-yl)methylamino)-9H-2-ylamino)pentan-2-ol
[18] 1,1,1,3,3,3-Hexafluoro-2-((9-isopropyl-6-(pyridine-3-ylmethylamino)-9H-purin-2-ylamino)methyl)propan-2-ol Another aspect of the invention relates to a compound of formula II, or a pharmaceutically acceptable salt thereof,

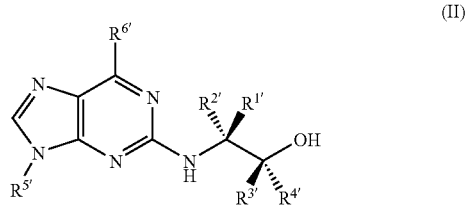

wherein:
at least one of $R^{1'}$, $R^{2'}$, $R^{3'}$ and $R^{4'}$ is haloalkyl and the remainder are each independently H, alkyl or haloalkyl;
$R^{5'}$ is alkyl or cycloalkyl or cycloalkyl-alkyl, each of which may be optionally substituted with one or more OH groups;
$R^{6'}$ is selected from cyclopropylamino, cyclopropylmethylamino, cyclobutylamino, cyclobutylmethylamino and

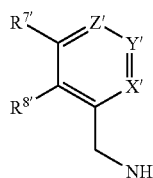

where X', Y' and Z' are each independently $CR^{9'}$, or one of X', Y' and Z' is N and the remainder are $CR^{9'}$; and
$R^{7'}$, $R^{8'}$ and each $R^{9'}$ are independently H, halo, alkyl or haloalkyl.
Preferably, for this aspect of the invention, $R^{5'}$ is isopropyl.
Preferably, for this aspect of the invention, $R^{6'}$ is

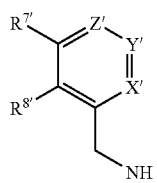

In one preferred embodiment, Y' is N, X' and Z' are CH, and $R^{7'}$ and $R^{8'}$ are both H.
In another preferred embodiment of the invention, one of $R^{1'}$ and $R^{2'}$ is H and the other is alkyl, or $R^{1'}$ and $R^{2'}$ are both H.
In one preferred embodiment of the invention, one of $R^{3'}$ and $R^{4'}$ is H and the other is $CF_3$.

In one especially preferred embodiment, the compound of the invention is selected from the following:

[15] 1,1,1-Trifluoro-3-(9-isopropyl-6-(pyridin-3-ylmethylamino)-9H-purin-2-ylamino)propan-2-ol
[16] 1,1,1-Trifluoro-3-(9-isopropyl-6-(pyridin-3-ylmethylamino)-9H-purin-2-ylamino)pentan-2-ol
[18] 1,1,1,3,3,3-Hexafluoro-2-((9-isopropyl-6-(pyridine-3-ylmethylamino)-9H-purin-2-ylamino)methyl)propan-2-ol A further aspect of the invention relates to a compound selected from the following:

[1] (2R,3S-3-(6-((4,6-Dimethylpyridin-3-ylmethylamino)-9-isopropyl-9H-purin-2-ylamino)pentan-2-ol
[2] 2R,3S-3-(9-isopropyl-6-((6-methylpyridin-3-yl)methylamino)-9H-purin-2-ylamino)pentan-2-ol
[3] 2R,3S-3-(6-(3-Chlorobenzylamino)-9-isopropyl-9H-purin-2-ylamino)pentan-2-
[4] 2R,3S-3-[6-(3-Fluorobenzylamino)-9-isopropyl-9H-purin-2-ylamino]-pentan-2-ol
[5] 2R,3S-3-(9-(Cyclopropylmethyl)-6-(pyridin-3-ylmethylamino)-9H-purin-2-ylamino)pentan-2-ol
[6] 2R,3S-3-(6-Cyclopropylamino)-9-isopropyl-9H-purin-2-ylamino)pentan-2-ol
[7] 2R,3S-3-(6-(Cyclopropylmethylamino)-9-isopropyl-9H-purine-2-ylamino)pentan-2-ol
[8] 2R,3S-3-(6-(Cyclobutylamino)-9-isopropyl-9H-purin-2-ylamino)pentan-2-ol
[9] 2R,3S-3-(9-Isopropyl-6-(pyridine-4-ylmethylamino)-9H-purin-2-ylamino)pentan-2-ol
[10] 2R,3S-3-(9-Isopropyl-6-(2,6-dimethylpyridine-4-ylmethylamino)-9H-purin-2-ylamino)pentan-2-ol
[11] 2R,3S-3-(9-Isopropyl-6-((6-(trifluoromethyl)pyridine-3-yl)methylamino)-9H-purin-2ylamino)pentan-2-ol
[12] 2R,3S-3-(9-Isopropyl-6-((6-methylpyridin-2-yl)methylamino)-9H-purin-2-ylamino)pentan-2-ol
[13] 2R,3S-3-(9-Isopropyl-6-((3-methylpyridin-2-yl)methylamino)-9H-purin-2-ylamino)pentan-2-ol
[14] (R)-1-(9-Isopropyl-6-(pyridin-3-ylmethylamino)-9H-purin-2-ylamino)propan-2-ol
[15] 1,1,1-Trifluoro-3-(9-isopropyl-6-(pyridin-3-ylmethylamino)-9H-purin-2-ylamino)propan-2-ol
[16] 1,1,1-Trifluoro-3-(9-isopropyl-6-(pyridin-3-ylmethylamino)-9H-purin-2-ylamino)pentan-2-ol
[17] 1,1,1-Trifluoro-3-(9-isopropyl-6-((6-(trifluoromethyl)pyridin-3-yl)methylamino)-9H-2-ylamino)pentan-2-ol
[18] 1,1,1,3,3,3-Hexafluoro-2-((9-isopropyl-6-(pyridine-3-ylmethylamino)-9H-purin-2-ylamino)methyl)propan-2-ol In one particularly preferred embodiment, the compound of the invention is selected from the following:

[3] 2R,3S-3-(6-(3-Chlorobenzylamino)-9-isopropyl-9H-purin-2-ylamino)pentan-2-
[4] 2R,3S-3-[6-(3-Fluorobenzylamino)-9-isopropyl-9H-purin-2-ylamino]-pentan-2-ol
[5] 2R,3S-3-(9-(Cyclopropylmethyl)-6-(pyridin-3-ylmethylamino)-9H-purin-2-ylamino)pentan-2-ol
[9] 2R,3S-3-(9-Isopropyl-6-(pyridine-4-ylmethylamino)-9H-purin-2-ylamino)pentan-2-ol
[14] (R)-1-(9-Isopropyl-6-(pyridin-3-ylmethylamino)-9H-purin-2-ylamino)propan-2-ol In one especially preferred embodiment of the invention, the compound is selected from: [1], [3], [4], [6], [7], [8], [9], [10] and [11]. More preferably, the compound is selected from [1], [3], [4], [6] and [11], even more preferably, the compound is [1] or [11].

Preferably, the compound of the invention exhibits at least a 3-fold increase in potency compared with seliciclib, more preferably at least a 4-fold or 5-fold increase in potency, even more preferably still, at least an 8-fold or 10-fold increase in potency.

In one especially preferred embodiment of the invention, the compound is (2R,3S-3-(6-((4,6-dimethylpyridin-3-ylmethylamino)-9-isopropyl-9H-purin-2-ylamino)pentan-2-ol [1], or a pharmaceutically acceptable salt or ester thereof.

Advantageously, compound [1] displays surprisingly high potency in cellular toxicity studies in a range of different cell lines compared to structurally related compounds known in the art. Further details of these studies are set forth in the accompanying examples (see in particular, Table 8).

Moreover, experiments have shown that contrary to structurally related compounds known in the art, compound [1] does not significantly inhibit CYP3A4. Again, these studies are described in more detail in the accompanying examples (see in particular, Table 5). Indeed, compound [1] does not appear to inhibit CYP3A4 until concentrations of greater than 20 μM, which is ~60 times its cellular $IC_{50}$. Since the $IC_{50}$ value for CYP3A4 inhibition for compound [1] inhibition is significantly above its cellular $IC_{50}$ (see Table 8), this indicates that at cytotoxic concentrations there should be no effect on CYP3A4 activity. This is significant because CYP3A4 is involved in the metabolism of a large number of medications. If CYP3A4 is inhibited by one drug this can lead to unexpected toxicity due to reduced metabolism of CYP3A4 substrates, thereby resulting in apparent increased levels of these agents.

Likewise, further experiments have shown that contrary to its structurally related analogues, compound [1] is not a substrate for the six CYP isoforms tested (see in particular, Table 6). This difference corresponds well with the observed difference in CYP inhibition discussed above. A common mechanism leading to CYP inhibition is if the compound is also a substrate for that CYP.

Accordingly, compound [1] is neither a substrate of, nor inhibitor of, CYP3A4, which imparts a significant, unexpected beneficial property over its structurally related analogues.

Pharmaceutical Compositions

A second aspect of the invention relates to a pharmaceutical composition comprising a compound of the invention admixed with a pharmaceutically acceptable diluent, excipient or carrier, or a mixture thereof. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the present invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes compounds of the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient for the treatment of malignancy.

Therapeutic Use

The compounds of the present invention have been found to possess anti-proliferative activity and are therefore believed to be of use in the treatment of proliferative disorders, such as cancers, leukaemias or other disorders associated with uncontrolled cellular proliferation such as psoriasis and restenosis.

As defined herein, an anti-proliferative effect within the scope of the present invention may be demonstrated by the ability to inhibit cell proliferation in an in vitro whole cell assay, for example using any of the cell lines A549, HeLa, HT-29, MCF7, Saos-2, CCRF-CEM, H460, HL-60 and K-562, or by showing kinase inhibition in an appropriate assay. These assays, including methods for their performance, are described in more detail in the accompanying Examples. Using such assays it may be determined whether a compound is anti-proliferative in the context of the present invention.

One preferred embodiment of the present invention therefore relates to the use of one or more compounds of the invention in the preparation of a medicament for treating a proliferative disorder.

As used herein the phrase "preparation of a medicament" includes the use of a compound of the invention directly as the medicament in addition to its use in a screening programme for further therapeutic agents or in any stage of the manufacture of such a medicament.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required. Preferably, the proliferative disorder is a cancer or leukaemia.

In another preferred embodiment, the proliferative disorder is psoriasis.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

A further aspect of the invention relates to a method of treating a proliferative disease, said method comprising administering to a mammal a therapeutically effective amount of a compound of the invention.

In a preferred embodiment of this aspect, the proliferative disorder is cancer or leukaemia.

In an even more preferred embodiment of this aspect, the compound is administered in an amount sufficient to inhibit at least one CDK enzyme.

Preferably, the compound of the invention is administered in an amount sufficient to inhibit at least one of CDK1, CDK2, CDK3, CDK4, CDK6, CDK7, CDK8 and/or CDK9.

More preferably, the compound of the invention is administered in an amount sufficient to inhibit at least one of CDK2 and/or CDK4.

Even more preferably, the CDK enzyme is CDK2.

In one preferred embodiment of this aspect, the compound is administered orally.

Another aspect of the invention relates to the use of a compound of the invention as an anti-mitotic agent.

Yet another aspect of the invention relates to the use of a compound of the invention for treating a neurodegenerative disorder.

Preferably, the neurodegenerative disorder is neuronal apoptosis.

Another aspect of the invention relates to the use of a compound of the invention as an antiviral agent.

Thus, another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of the invention is administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

The compounds of the invention are also useful in the preparation of medicaments for the treatment of various ophthalmic disorders. Preferably, the ophthalmic disorder is glaucoma, exudative age-related macular degeneration (AMD) or proliferative diabetic retinopathy (PDR).

The disease state referred to as glaucoma is characterized by a permanent loss of visual function due to irreversible damage to the optic nerve. The several morphologically or functionally distinct types of glaucoma are typically characterized by elevated intraocular pressure (IOP), which is considered to be causally related to the pathological course of the disease. Ocular hypertension is a condition wherein intraocular pressure is elevated, but no apparent loss of visual function has occurred; such patients are considered to be a high risk for the eventual development of the visual loss associated with glaucoma. GSK-3 inhibitors are useful for the treatment of eye diseases such as glaucoma. It has been shown that a component of the Wnt signalling pathway, frizzled related protein (FRP), is differentially expressed in a number of glaucomatous trabecular meshwork cell lines and can disrupt the normal signalling cascade causing an increase in outflow resistance and development of elevated IOP. Hellberg M. R et al (US20040186159) have shown that through the interaction of GSK-3 with components of the Wnt signalling pathway, inhibition of GSK-3 by pharmacological agents can circumvent the FRP mediated antagonism of the Wnt signaling pathway caused by the elevated levels of FRP and counteract the increase in outflow resistance that results from the increase in production of FRP in individuals with glaucoma.

CTGF is a secreted cytokine which is known to increase extracellular matrix (ECM) production, primarily via increased deposition of collagen I and of fibronectin. Overexpression of CTGF has previously been implicated as a major causative factor in conditions such as scleroderma, fibroproliferative diseases, scarring, etc. in which there is an overaccumulation of ECM components. An overaccumulation of extracellular matrix materials in the region of the trabecular meshwork (TM) is also a hallmark of many forms of glaucoma; such increases are believed to lead to increased resistance to aqueous outflow, and therefore elevated intraocular pressures. Fleenor D L et al (US20050234075) have shown that GSK-3 inhibitors and CDK inhibitors can inhibit both basal and TGF.beta.2-induced CTGF expression in human TM cells therefore compounds of the current invention are useful for the treatment of glaucoma.

The compounds of the invention are also useful in the treatment of AMD and PDR. Exudative age-related macular degeneration (AMD) and proliferative diabetic retinopathy (PDR) are the major causes of acquired blindness in developed countries and are characterized by pathologic posterior segment neovascularization in the eye. The inciting cause in both exudative AMD and PDR is still unknown, however, the elaboration of various proangiogenic growth factors appears to be a common stimulus. Soluble growth factors, such as vascular endothelial growth factor (VEGF), platelet-derived growth factor (PDGF), basic fibroblast growth factor (bFGF or FGF-2), insulin-like growth factor 1 (IGF-1), angiopoietins, etc., have been found in tissues and fluids removed from patients with pathologic ocular angiogenesis. Inhibition or blockade of the activity of these growth factors and of other intracellular enzymes such as aurora kinases has been shown to have an antiangiogenic effect. Thus compounds of the current invention are useful for treating ophthalmic diseases characterised by neovascularization.

Another aspect of the invention relates to the use of compounds of the invention, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M. X.; Bjorbaek, C.; Vestergaard, H.; Hansen, T.; Cohen, P. T.; Pedersen, O. *Diabetes*, 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. *Diabetes*, 2000, 49, 263].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of the invention, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [Goedert, M. *Curr. Opin. Gen. Dev.*, 2001, 11, 343].

Another aspect of the invention relates to the use of compounds of the invention, or pharmaceutically acceptable salts thereof, in the preparation of a medicament for treating bipolar disorder.

Yet another aspect of the invention relates to the use of compounds of the invention, or pharmaceutically acceptable salts thereof, in the preparation of a medicament for treating a stroke.

Reducing neuronal apoptosis is an important therapeutic goal in the context of head trauma, stroke, epilepsy, and motor neuron disease [Mattson, M. P. Nat. Rev. Mol. Cell. Biol., 2000, 1, 120]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of the invention, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated β-catenin [DasGupta, R.; Fuchs, E. Development, 1999, 126, 4557], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound according to the invention, or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [Sunkel et al., *J. Cell Sci.*, 1988, 89, 25] and polo was found to encode a mitotic kinase [Llamazares et al., *Genes Dev.*, 1991, 5, 2153]. In humans, there exist three closely related PLKs [Glover et al., *Genes Dev.*, 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., *Proc. Natl. Acad. Sci. USA*, 1998, 95, 9301; Leung et al., *Nat. Struct. Biol.*, 2002, 9, 719], mediation of interactions with other proteins [Kauselmann et al., *EMBO J.*, 1999, 18, 5528], or may constitute part of an autoregulatory domain [Nigg, *Curr. Opin. Cell Biol.*, 1998, 10, 776]. Furthermore, the polo box-dependent PLK1 activity is required for proper metaphase/anaphase transition and cytokinesis [Yuan et al., *Cancer Res.*, 2002, 62, 4186; Seong et al., *J. Biol. Chem.*, 2002, 277, 32282].

Studies have shown that human PLKs regulate some fundamental aspects of mitosis [Lane et al., *J. Cell. Biol.*, 1996, 135, 1701; Cogswell et al., *Cell Growth Differ.*, 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., *Proc. Natl. Acad. Sci. USA*, 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., *Nature*, 2001, 410, 215; Roshak et al., *Cell. Signalling*, 2000, 12, 405], DNA-damage checkpoint activation [Smits et al., *Nat. Cell Biol.*, 2000, 2, 672; van Vugt et al., *J. Biol. Chem.*, 2001, 276, 41656], regulation of the anaphase promoting complex [Sumara et al., *Mol. Cell*, 2002, 9, 515; Golan et al., *J. Biol. Chem.*, 2002, 277, 15552; Kotani et al., *Mol. Cell*, 1998, 1, 371], phosphorylation of the proteasome [Feng et al., *Cell Growth Differ.*, 2001, 12, 29], and centrosome duplication and maturation [Dai et al., *Oncogene*, 2002, 21, 6195].

Specifically, initiation of mitosis requires activation of M-phase promoting factor (MPF), the complex between the cyclin dependent kinase CDK1 and B-type cyclins [Nurse, *Nature*, 1990, 344, 503]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, *Nat. Rev. Mol. Cell Biol.*, 2001, 2, 21]. In interphase, cyclin B localizes to the cytoplasm [Hagting et al., *EMBO J.*, 1998, 17, 4127], it then becomes phosphorylated during prophase and this event causes nuclear translocation [Hagting et al., *Curr. Biol.*, 1999, 9, 680; Yang et al., *J. Biol. Chem.*, 2001, 276, 3604]. The nuclear accumulation of active MPF during prophase is thought to be important for initiating M-phase events [Takizawa et al., *Curr. Opin. Cell Biol.*, 2000, 12, 658]. However, nuclear MPF is kept inactive by WEE1 unless counteracted by CDC25C. The phosphatase CDC25C itself, localized to the cytoplasm during interphase, accumulates in the nucleus in prophase [Seki et al., *Mol. Biol. Cell*, 1992, 3, 1373; Heald et al., *Cell*, 1993, 74, 463; Dalal et al., *Mol. Cell. Biol.*, 1999, 19, 4465]. The nuclear entry of both cyclin B [Toyoshima-Morimoto et al., *Nature*, 2001, 410, 215] and CDC25C [Toyoshima-Morimoto et al., *EMBO Rep.*, 2002, 3, 341] are promoted through phosphorylation by PLK1 [Roshak et al., *Cell. Signalling*, 2000, 12, 405]. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang et al., *Mol. Cell. Biol.*, 2002, 22, 3450]. PLK2 is the least well understood homologue of the three PLKs. Both PLK2 and PLK3 may have additional important post-mitotic functions [Kauselmann et al., *EMBO J.*, 1999, 18, 5528].

Another aspect of the invention relates to the use of a compound of the invention for inhibiting a protein kinase.

In a preferred embodiment of this aspect, the protein kinase is a cyclin dependent kinase. Preferably, the protein kinase is CDK1, CDK2, CDK3, CDK4, CDK6, CDK7, CDK8 or CDK9, more preferably CDK2.

A further aspect of the invention relates to a method of inhibiting a protein kinase, said method comprising contacting said protein kinase with a compound of the invention.

In a preferred embodiment of this aspect, the protein kinase is a cyclin dependent kinase, even more preferably CDK2.

Assays

Another aspect of the invention relates to the use of a compound as defined hereinabove in an assay for identifying further candidate compounds that influence the activity of one or more of a cyclin dependent kinase, an aurora kinase, a GSK and/or a PLK enzyme.

Preferably, the assay is capable of identifying candidate compounds that are capable of inhibiting one or more of a cyclin dependent kinase, an aurora kinase, a GSK and/or a PLK enzyme.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a cyclin dependent kinase, an aurora kinase, a GSK or a PLK enzyme in the presence of a known substrate of said CDK enzyme and detecting any change in the interaction between said kinase and said known substrate.

A further aspect of the invention provides a method of detecting the binding of a ligand to a cyclin dependent kinase, an aurora kinase, a GSK or a PLK enzyme, said method comprising the steps of:
(i) contacting a ligand with a cyclin dependent kinase, an aurora kinase, a GSK or a PLK enzyme in the presence of a known substrate of said kinase;
(ii) detecting any change in the interaction between said kinase and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more CDK enzymes.

The present invention is further described by way of the following examples, and with reference to the following figure, wherein.

EXAMPLES

General

Figure 1:
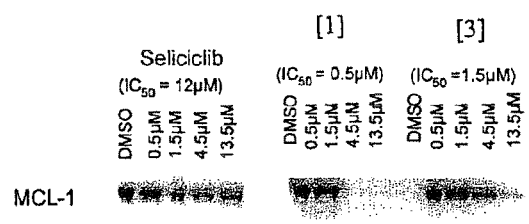
FIG. 1 shows downregulation of Mcl-1 by the compounds of the invention. H460 cells were treated for 24 hours with various concentrations of the compounds and analysed by Western blotting for changes in the level of Mcl-1.

Chemicals and solvents were purchased from commercial sources and were used as received unless otherwise stated. THF and $Et_2O$ were dried by heating under reflux with sodium-benzophenone under $N_2$ and collected by distillation. Toluene was dried by heating under reflux over sodium under $N_2$. $CH_2Cl_2$ was dried by heating under reflux over $CaH_2$ under $N_2$. The microwave generator used was a CEM "Discover" model, with a circular single mode cavity design, that focuses the microwave radiation on the sample tube. TLC (thin-layer chromatography) was performed using glass plates coated with silica gel G60 (0.25 cm). Developed plates were air dried and analysed under a UV lamp (254/365 nm). Anhydrous $MgSO_4$ was used as a standard drying agent for organic solutions unless otherwise stated. Flash column chromatography was performed using Fluorochem silica gel (35-70 μm). Melting points (mp) were determined with an Electrothermal 9100 capillary melting point apparatus and are uncorrected. The abbreviation (dec) denotes a decomposition point. $^1$H-NMR spectra were recorded on a Bruker Avance 300 (300.1 MHz) or a Varian Gemini 2000 (300 MHz) spectrometer using the deuterated solvent as the lock and the residual solvent as the internal reference in all cases. $^{13}$C-NMR spectra using the PENDANT sequence were recorded on a Bruker Avance 300 (75.5 MHz) spectrometer. All other $^{13}$C-spectra were recorded on a Varian Gemini 2000 (75.5 MHz) spectrometer using composite pulse $^1$H decoupling. Coupling constants (J) are quoted to the nearest 0.1 Hz. The following abbreviations are used: s, singlet; d, doublet; t, triplet; q, quartet; qu, quintuplet; m, multiplet and br, broad. Elemental microanalyses were performed by Mrs S Williamson, School of Chemistry, Purdie Building, University of St. Andrews, UK. Results obtained were within 0.4% of calculated values. Electrospray mass spectra (ESI) were recorded on a Micromass LCT mass spectrometer, coupled to a Waters 2975 HPLC. Analytical RP-HPLC was performed using a Dionex ASI-100 automated sample injector coupled to a Dionex P580 pump. A Phenomenex column (150×4.60 mm, Synergi 4μ hydro-RP 80 Å), kept at a temperature of 25° C. was used for analytical purposes. The HPLC unit was controlled using Chromeleon software. Linear gradient elution using $H_2O$/MeCN systems (containing 0.1% $CF_3COOH$) at

Synthesis (2R,3S)-3-Amino-pentan-2-ol was prepared by one or other of two routes differing in the protecting group used for the amine.

Route 1 Employed Trityl as the Protecting Group

(S)-2-(Tritylamino)butan-1-ol

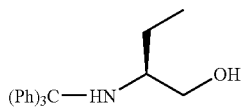

To a stirred solution of (S)-(+)-2-aminobutan-1-ol (10 g, 112.18 mmol) in dichloromethane (DCM, 250 ml) under an argon atmosphere at room temperature, was added diisopropylethylamine (DIEA, 19.4 ml, 112.18 mmol) followed by trityl chloride (31.2 g, 112.18 mmol). The reaction mixture was stirred at this temperature for 48 h, when TLC (hexane:ether:MeOH; 55:40:5) indicated that the reaction had gone to completion. The solvent was evaporated in vacuo and the residue taken up in ethyl acetate. The organic solution was washed with water (2×), dried over sodium sulphate. The solvent was removed to afford (S)-2-(trityl-amino)-butan-1-ol as a light yellow oil; Yield: 33 g (89%). $^1$H-NMR (CDCl$_3$, 250 MHz): δ 0.72 (3 H, t, J=7.5 Hz, —NHCH(CH$_2$CH$_3$)CH$_2$OH), 1.15-1.10 (m, 2H, —NHCH(CH$_2$CH$_3$)CH$_2$OH), 2.05 (1 H, s, br, NH), 2.24 (1 H, s, br, OH), 2.62-2.54 (m, 1H, —NHCH(CH$_2$CH$_3$)CH$_2$OH), 3.17-3.08 (1 H m, —NHCH(CH$_2$CH$_3$)CHHOH), 3.35-3.29 (1 H, m, NHCH(CH$_2$CH$_3$)CHHOH), 7.37-7.2 (12H, m, ArH), 7.65-7.58 (3 H, m, ArH); δ$_C$ (250 MHz, CDCl$_3$) 146.86 (C), 129.43 (6×CH), 127.90 (6×CH), 126.48 (3×CH), 71.27 (C), 62.72 (CH$_2$), 48.91 (CH), 24.55 (CH$_2$), 10.47 (CH$_3$)

(S)-2-(Tritylamino)butyraldehyde

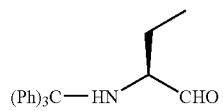

To a stirred solution of dry dimethylsulfoxide (2.4 ml, 2.8 eq, 33.82 mmol) in dry dichloromethane (30 ml) under an argon atmosphere at −78° C., was added oxalyl chloride (2M solution in DCM, 8.45 ml, 1.40 eq, 16.9 mmol), dropwise. The reaction mixture was stirred at −78° C. for 1 h, after which time a solution of (S)-2-(trityl-amino)-butan-1-ol (4 g, 1 eq, 12.07 mmol) in DCM (30 ml) was added dropwise with stiffing. The reaction mixture was stirred at this temperature for 2 h after which was added a solution of triethylamine (TEA, 8.4 ml, 5 eq, 60.27 mmol) in DCM (30 ml), and the solution allowed to warm to room temperature over 1 h. The reaction mixture was diluted with more DCM (100 ml) and washed with water (250 ml). The aqueous phase was extracted with DCM (3×50 ml), and the combined organic phase washed with brine (50 ml), dried (Na$_2$SO$_4$) and evaporated in vacuo. The residue was purified by flash silica chromatography (ethyl acetate:Hexane 1:4) to afford (S)-2-(trityl-amino)-butyraldehyde as a light yellow oil; Yield: 3.64 g (91%). $^1$H-NMR (CDCl$_3$, 250 MHz): δ 0.95 (3 H, t, J=7.5 Hz, —NHCH(CH$_2$CH$_3$)CHO), 1.72-1.52 [2 H, m, NHCH(CH$_2$CH$_3$)CHO], 2.76 (1 H, s, br, —NH), 3.41-3.36 [1 H, m, NHCH(CH$_2$CH$_3$)CHO], 7.35-7.17 (12H, m, ArH), 7.67-7.51 (3 H, m, ArH), 9.05 (1 H, s, NHCH(CH$_2$CH$_3$)CHO). δ$_C$ (250 MHz, CDCl$_3$) 202.95 (CO), 146.23 (C), 129.23 (6×CH), 127.96 (6×CH), 126.85 (3×CH), 71.13 (C), 62.62 (CH), 24.78 (CH$_2$), 10.48 (CH$_3$)

(2R,3S)-3-(Tritylamino)pentan-2-ol

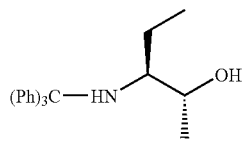

To a stirred suspension of CuBr.SMe$_2$ (3 g, 14.6 mmol) in anhydrous ether (100 ml) under an argon atmosphere at −78° C., was added methyl lithium (1.6M in ether, 16.5 ml, 4.0 eq, 26.5 mmol) dropwise and the solution allowed to warm to room temperature over 1 h. The mixture was recooled to −78° C., and a solution of (S)-2-(trityl-amino)-butyraldehyde (2.2 g, 6.62 mmol) in ether (25 ml) was added dropwise with stiffing. The reaction mixture was stirred at this temperature for 2 h then allowed to warm to room temperature over 1 h. A saturated aqueous solution of NH$_4$Cl (50 ml) was added and the two layers separated. The organic phase was washed with brine (50 ml), dried (MgSO$_4$) and evaporated in vacuo. The residue was purified by flash silica gel column chromatography, eluted with hexane:ethyl acetate (80:20) to afford (2R, 3S)-3-(trityl-amino)-pentan-2-ol as a light yellow oil; Yield: 1.5 g (66%). (75% de 2R, 3S: 25% de 2S, 3S). $^1$H-NMR (d$_6$-DMSO, 250 MHz): δ 0.0.47+0.55 (2×t, J=7.50+7.26 Hz —NHCH(CH$_2$CH$_3$)CH(CH$_3$)OH), 0.99-1.12 (m, 5 H, —NHCH(CH$_2$CH$_3$)CH(CH$_3$)OH), 2.01 (1 H, m, —NHCH(CH$_2$CH$_3$)CH(CH$_3$)OH), 3.22-3.43 (m, 1H, —NHCH(CH$_2$CH$_3$) CH(CH$_3$)OH), 4.41 [1 H, d, J=3.3, NHCH(CH$_2$CH$_3$)CH(CH$_3$)OH], 7.14-7.56 (15 H, m, ArH). δ$_C$ (250 MHz, CDCl$_3$) 146.88 (C), 128.97 (6×CH), 127.83 (6×CH), 126.43 (3×CH), 71.03 (C), 68.13 (CH), 58.77 (CH), 23.09 (CH$_2$), 17.88 (CH$_3$), 10.47 (CH$_3$)

(2R,3S)-3-Amino-pentan-2-ol

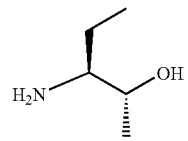

To a stirred solution of (2R,3S)-3-(trityl-amino)-pentan-2-ol (1.64 g, 4.75 mmol) in dichloromethane (20 ml) under an argon atmosphere at room temperature, was added trifluoroacetic acid (10 ml) dropwise, and the solution was stirred at this temperature for 1 h. The solvent was evaporated in vacuo and the residue was precipitated from ether (15 ml) with hexane (150 ml) with stiffing to give a yellow oil. The solvent was decanted from the oil, and the oil was washed with hexane (30 ml) and dried in vacuo to afford (2R,3S)-3-amino-pentan-2-ol as a light yellow oil; Yield: 0.30 g (98%). (75% de 2R, 3S: 25% de 2S, 3S). $^1$H-NMR (d$_6$-DMSO, 250 MHz): δ

0.913+0.923 (2×t, 3 H, J=7.50+7.50 Hz, NH₂CH(CH₂CH₃)CH(CH₃)OH), 1.11+1.18 (3 H, 2×d, J=6.48+6.48 Hz, NH₂CH(CH₂CH₃)CH(CH₃)OH), 1.41-1.65 (2 H, m, NH₂CH(CH₂CH₃)CH(CH₃)OH), 2.76+2.93 [2×1 H, m, NH₂CH(CH₂CH₃)CH(CH₃)OH], 3.61-3.69+3.80-3.90 [2×1 H, m, NH₂CH(CH₂CH₃) CH(CH₃)OH], 7.73 (2 H, s, br, NH₂).
Route 2 Protected the Amine by Dibenzylation (S)-2-(Dibenzylamino)butan-1-ol

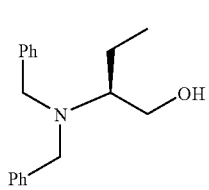

To a stirred solution of (S)-(+)-2-aminobutan-1-ol (5 g, 56.18 mmol) in dry acetonitrile (100 ml) was added dry powdered potassium carbonate (31 g, 224.72 mmol) followed by benzyl bromide (19 g, 111.11 mmol). The reaction was stirred at room temperature for 24 h. The solvent was removed under vaccuo and the residue was taken up in ethyl acetate (100 ml) and water (100 ml). The organic phase was washed again with water, dried (Na₂SO₄) and concentrated to provide the pure product as slightly yellow oil (14.5 g, 97.3%). δ$_H$ (250 MHz, CDCl₃) 0.98 (3 H, t, J 7.5, CHCH₂CH₃), 1.38-1.2 (1H, m, CHCHHCH₃), 1.94-1.78 (1 H, m, CHHCH₃), 2.83-2.71 (1 H, m, CHCHHCH₃), 3.22 (1 H, s, b, OH), 3.65-3.4 (2 H, m, CH₂OH), 3.47 (2 H, d, J 17.5, 2×CHHPh), 3.94 (2H, d, J 17.5, 2×CHHPh), 7.46-7.26 (10 H, m, 2×C₆H₅); δ$_C$ (250 MHz, CDCl₃) 139.42 (2×C), 129.1 (2×CH), 128.52 (2×CH), 127.25 (2×CH), 61.97 (CH), 60.67 (CH₂), 53.23 (CH₂), 17.92 (CH₂), 11.83 (CH₃); m/z 270.2 (M+H)

(S)-2-(Dibenzylamino)butanal

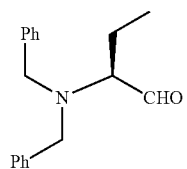 [SMILES: CC[C@@H](C=O)N(Cc1ccccc1)Cc1ccccc1]

A 2M solution of oxalyl chloride in dichloromethane (3.18 ml, 6.36 mmol) was cooled to −78 0° C. and diluted with dry dichloromethane (20 ml) under dry nitrogen. A solution of dimethylsulfoxide (1 g, 12.72 mmol) in anhydrous dichloromethane was added dropwise to the cooled stirred solution. The reaction was stirred for a further 1 h after completion of addition. A solution of (S)-2-(dibenzylamino) butan-1-ol (1.43 g, 5.3 mmol) in dichloromethane was added over 5 minutes. After 10 minutes, diisopropylethylamine (2.73 g, 21.2 mmol) was added. The reaction was allowed to warm to room temperature and left stiffing for 1 h. It was cooled to 0° C. and ethyl acetate/water (50 ml: 50 ml) was added. The organic layer was washed with water (50 ml), brine (50 ml) dried (MgSO₄) and concentrated. The product was purified by flash silica column chromatography (ethyl acetate:Hexane 1:4) to provide the pure product (1.28 g, 90.5%). δ$_H$ (250 MHz, CDCl₃) 0.88 (3 H, t, J 7.5, CHCH₂CH₃), 1.77-1.54 (2 H, m, CH₂CH₃), 2.99 (1 H, t, J 7.5, CHCH₂CH₃), 3.74-3.57 (4 H, m, 2×CH₂Ph), 7.31-7.11 (10 H, m, 2×C₆H₅) 9.64 (1 H, s, CHO); δ$_C$ (250 MHz, CDCl₃) 203.9 (CO), 139.33 (2×C), 128.99 (4×CH), 128.45 (4×CH), 127.3 (2×CH), 68.46 (CH), 54.85 (CH₂), 17.44 (CH₂), 11.83 (CH₃); m/z 268.2 (M+H)

(2R,3S)-3-(Dibenzylamino)pentan-2-ol

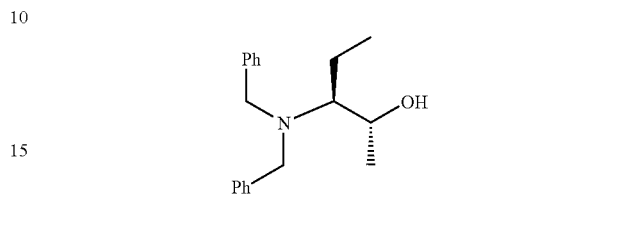

To a stirred suspension of CuBr.SMe₂ (1.54 g, 7.5 mmol) in anhydrous ether under an argon atmosphere at −78° C., was added methyllithium (1.6M in ether, 9.4 ml, 15 mmol) dropwise. After the addition was complete, the reaction was allowed to warm to room temperature. The reaction was recooled to −78° C. and a solution of (S)-2-(dibenzylamino) butanal (1 g, 3.75 mmol) in ether (20 ml) was added dropwise. After the addition, continued stirring for 2 h The reaction was then quenched with a saturated aqueous solution of NH₄Cl (10 ml). The reaction mixture was extracted with ether (2×30 ml) and the combined organic phase washed with brine (20 ml), dried (MgSO₄) and evaporated in vacuo. The residue was purified by flash silica gel gradient column chromatography, eluted with hexane:ethyl acetate (100:0→80:20) to afford the product as a light yellow oil (0.95 g, 89%) as the only isomer. δ$_H$ (250 MHz, CDCl₃) 1.05 (3 H, t, J 7.5, CHCH₂CH₃), 1.25 [3 H, d, J 7.5, CH(CH₃)OH], 1.6-1.49 (1 H, m, CHHCH₃), 1.88-1.73 (1 H, m, CHHCH₃), 2.41 (1 H, s, br, OH), 2.66-2.59 (1 H, m, CHCH₂CH₃), 3.85-3.65 (4 H, m, 2×CH₂Ph), 4.05-3.9 (1 H, m, CHOH), 7.41-7.25 (10 H, m, ArH) δ$_C$ (250 MHz, CDCl₃) 140.05 (2×C), 128.98 (4×CH), 128.37 (4×CH), 127.3 (2×CH), 66.81 (CH), 63.65 (CH), 55.41 (CH₂), 20.63 (CH₃) 18.44 (CH₂), 12.5 (CH₃)

Example 1

2-Chloro-4,6-dimethylnicotinonitrile

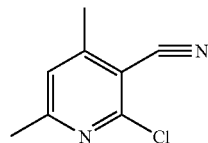

4,6-Dimethyl-2-oxo-1,2-dihydropyridine-3-carbonitrile (5 g, 34 mmol) was added to phosphorus oxychloride (20 ml). The reaction was stirred at reflux for 2 h, after which it was seen complete. Volatiles were removed and the residue triturated with petrol. The resultant solid was filtered off and washed with hexane, and dried to give a pure white solid (5.1 g, 90%). δ$_H$ (250 MHz, CDCl₃) 2.55 (3 H, s, CH₃), 2.57 (3 H, s, CH₃), 7.09 (1 H, s, ArH); δ$_C$ (250 MHz, CDCl₃) 162.64 (C), 154.39 (C), 152.26 (C), 123.22 (CH), 114.28 (C), 108.31 (C), 24.5 (CH$_3$), 20.54 (CH$_3$); m/z 189 (M+Na)

4,6-Dimethylpyridin-3-ylmethyl carbamic acid t-butyl ester

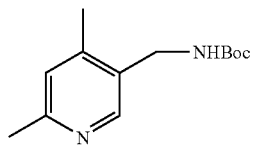

2-Chloro-4,6-dimethyl-nicotinonitrile (5 g, 30.1 mmol) was dissolved in 10% acetic acid/ethanol (30 ml). 10% palladium over charcoal catalyst (0.5 g) was added and the reaction stirred under an atmosphere of hydrogen for 24 h. at 60° C. The mixture was filtered through a pad of celite. Volatiles were removed and the crude residue dissolved in dichloromethane (30 ml). To the stirred solution was then added triethylamine (5 ml) followed by di-tert-butyldicarbonate (6.5 g, 30 mmol). After 3 h, the solvent was removed and the residue dissolved in ethyl acetate. It was washed with water (50 ml), saturated bicarbonate (50 ml), dried and evaporated. The crude product was purified by silica gel flash column chromatography (ethyl acetate:hexane 1:2) to provide 1.4 g of pure title compound (20% yield). $\delta_H$ (250 MHz, CDCl$_3$) 1.43 (9 H, s, 3×CH$_3$) 2.19 (3H, s, CH$_3$), 2.38 (3 H, s, CH$_3$), 4.19 (2 H, s, br, ArCH$_2$NH), 6.84 (1 H, s, ArH), 8.15 (1H, s, ArH); $\delta_C$ (250 MHz, CDCl$_3$) 157.41 (CO), 155.63 (C), 148.93 (CH), 145.91 (C), 129.51 (C), 124.76 (CH), 79.44 (C), 46.12 (CH$_2$), 28.32 (3×CH$_3$), 23.74 (CH$_3$), 18.97 (CH$_3$); m/z 237.2 (M+H)

(4,6-Dimethylpyridin-3-ylmethyl)-(2-fluoro-9H-purin-6-yl)-amine

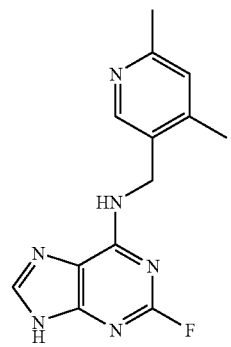 [SMILES: Cc1cc(C)c(CNc2nc(F)nc3[nH]cnc23)cn1]

To a stirred solution of 6-chloro-2-fluoropurine (0.83 g, 4.9 mmol) in n-BuOH (50 ml) under an argon atmosphere at 0° C., was added DIEA (2.5 ml, 14.7 mmol) followed by (4,6-dimethylpyridine-3-yl)methanamine (1 g, 7.35 mmol). The reaction mixture was stirred at this temperature for 1 h and then allowed to return to room temperature and stirred for 4 h, it was still seen incomplete, hence heated the reaction to 100° C. and left at that temperature for 2 h. The solvent was evaporated in vacuo and the residue was purified by gradient flash column chromatography on silica gel, eluted with CHCl$_3$:MeOH (100:0→90:10), to afford the product as a white solid; Yield: 0.86 g (65%); $\delta_H$ (250 MHz, CDCl$_3$) 2.35 (3 H, s, CH$_3$), 2.39 (3 H, s, CH$_3$), 4.61 (2 H, s, br, NHCH$_2$), 7.07 (1 H, s, ArH), 8.13 (1 H, s, ArH), 8.33 (1 H, s, ArH), 8.69 (1 H, s, br, NH); $\delta_C$ (250 MHz, CDCl$_3$) 161.2 (C), 158.57 (C), 156.08 (C), 150 (C), 148.08 (CH), 148.14 (CH), 147.9 (CH), 145.93 (C), 129.92 (C), 129.76 (C), 124.37 (CH), 41.7 (CH$_2$), 23.17 (CH$_3$), 18.14 (CH$_3$); m/z 273.2 (M+H)

(4,6-Dimethylpyridin-3-ylmethyl)-(2-fluoro-9-isopropyl 9H-purin-6-yl)-amine

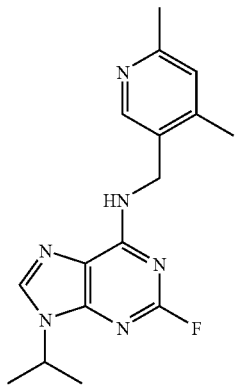 [SMILES: Cc1cc(C)c(CNc2nc(F)nc3c2ncn3C(C)C)cn1]

To a stirred solution of (4,6-dimethyl-pyridin-3-ylmethyl)-(2-fluoro-9H-purin-6-yl)-amine (0.6 g, 1.9 mmol) in DMF (10 ml) under an argon atmosphere, at RT, was added K$_2$CO$_3$ (powdered, anhydrous, 1.77 g, 5 eq, 13 mmol) followed by 2-bromopropane (1.8 ml, 10 eq, 19 mmol). The reaction mixture was stirred at RT for 24 h, when TLC (CHCl$_3$:MeOH; 90:10) indicated that the reaction had gone to completion. The solvent was evaporated in vacuo and the residue partitioned between water (50 ml) and ethyl acetate (50 ml), the aqueous phase was separated and extracted with more EtOAc (2×50 ml). The bulked organic phase was washed with brine (50 ml), dried (MgSO$_4$) and evaporated in vacuo, and the residue was purified by gradient column chromatography on silica gel, eluted with CHCl$_3$:MeOH (100:0→95:5), to provide the product as a yellow film (0.4 g, 59%). $\delta_H$ (250 MHz, CDCl$_3$) 1.52 [6 H, d, J 7.5 CH(CH$_3$)$_2$] 2.27 (3H, s, CH$_3$), 2.45 (3 H, s, CH$_3$), 4.73-4.62 (3H, m, NHCH$_2$ and CH[CH$_3$]$_2$), 6.91 (1 H, s, ArH), 7.12 (1 H, NH), 7.47 (1H, s, ArH), 8.32 (1 H, s, ArH); $\delta_C$ (250 MHz, CDCl$_3$) 160.77 (C), 157.89 (C), 157.43 (C), 156.12 (C), 155.79 (C), 149.14 (CH), 137.7 (CH), 128.7 (C), 129.76 (C), 124.83 (CH), 47.2 (CH), 40.14 (CH$_2$), 23.9 (CH$_3$), 22.47 (2×CH$_3$), 18.54 (CH$_3$); m/z 315.3 (M+H)

(2R,3S-3-(6-((4,6-Dimethylpyridin-3-ylmethylamino)-9-isopropyl-9H-purin-2-ylamino)pentan-2-ol [1]

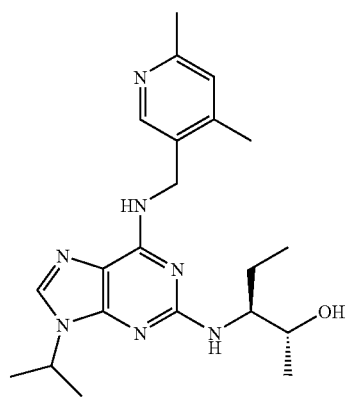 [SMILES: CC[C@H](Nc1nc(NCc2cnc(C)cc2C)c2ncn(C(C)C)c2n1)[C@@H](C)O]

To a stirred solution of (4,6-dimethyl-pyridin-3-ylmethyl)-(2-fluoro-9-isopropyl-9H-purin-6-yl)-amine (300 mg, 0.84 mmol) in n-BuOH/DMSO (5 ml, 4:1) at room temperature under an argon atmosphere was added DIEA (1.7 ml, 10 eq, 8.4 mmol) followed by (2R,3S)-3-amino-pentan-2-ol (0.5 g, 4.8 mmol) The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between ethyl acetate (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by flash gradient column chromatography on silica gel eluted with CHCl$_3$:MeOH (100:0→95:5), to afford 55 mg of pure title compound (12%). $\delta_H$ (250 MHz, CDCl$_3$) 0.95 (3 H, t, J 7.5, CHCH$_2$CH$_3$), 1.06 (3 H, d, J 7.5, CHCH$_3$OH) 1.48 [6 H, d, J 7.5 CH(CH$_3$)$_2$], 2.24 (3 H, s, CH$_3$), 2.4 (3 H, s, CH$_3$), 3.92-3.82 (2 H, m, NHCH$_2$), 4.67-4.45 (3 H, m, CHEtCHMeOH), 6.15 (1 H, s, br, NH), 6.87 (1 H, s, ArH), 7.37 (1 H, ArH), 8.31 (1 H, s, ArH); $\delta_C$ (250 MHz, CDCl$_3$) 160.11 (C), 157.68 (C), 154.57 (C), 149.42 (CH), 146.38 (C), 134.54 (CH), 129.24 (C), 124.84 (CH), 71.52 (CH), 59.65 (CH), 46.47 (CH), 40.33 (CH$_2$), 24.94 (CH$_2$), 23.89 (CH$_3$), 23.52 (2×CH$_3$), 17.37 (CH$_3$), 12.57 (CH$_3$); m/z 398.3 (M+H)

Example 2

2-Fluoro-N-((6-methylpyridin-3-yl)methyl)-9H-purin-6-amine

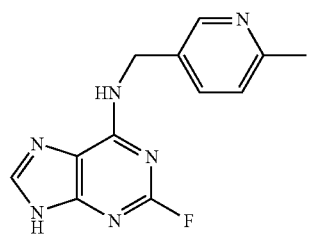 [SMILES: Cc1ccc(CNc2nc(F)nc3[nH]cnc23)cn1]

To a stirred solution of 6-chloro-2-fluoropurine (0.4 g, 2.3 mmol) in n-BuOH (50 ml) under an argon atmosphere at 0° C., was added DIEA (2.5 ml, 14.7 mmol) followed by (6-methylpyridin-3-yl)methanamine (0.36 g, 2.95 mmol). The reaction mixture was stirred at this temperature for 1 h and then allowed to return to room temperature and stirred for 4 h, it was still seen incomplete, hence heated the reaction to 100° C. and left at that temperature for 8 h. The solvent was evaporated in vacuo and the residue was purified by gradient column chromatography on silica gel, eluted with CHCl$_3$:MeOH (100:0→90:10), to afford the product as a white solid; Yield: 0.38 g (65%) $\delta_H$ CDCl$_3$, 250 MHz) 2.44 (3 H, s, CH$_3$), 3.66-3.57 (2 H, m, NHCH$_2$), 4.63 (1H, s, br, NH), 7.25 (1 H, d, J 7.5, ArH), 7.71 (1 H, dd, J 2.5, 7.5, ArH), 8.14 (1 H, s, ArH), 8.49 (1 H, s, ArH), 9.07 (1 H, s, br, NH); $\delta_C$ (CDCl$_3$, 250 MHz) 159.12 (C), 158.62 (C), 157.61 (C), 155.56 (C), 147.44 (CH), 146.99 (CH), 136.32 (C), 123.05 (2×CH), 119.42 (C), 41.64 (CH$_2$), 18.47 (CH$_3$); m/z 259.2 (M+H)

2-Fluoro-9-isopropyl-N-((6-methylpyridin-3-yl)methyl)-9H-purin-6-amine

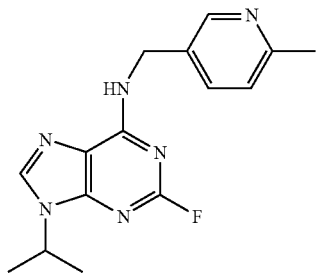 [SMILES: Cc1ccc(CNc2nc(F)nc3c2ncn3C(C)C)cn1]

To a stirred solution of 2-fluoro-N-(6-methylpyridin-3-yl)methyl-9H-purin-6-amine (0.3 g, 1.17 mmol) in dimethylformamide (10 ml) at room temperature under an argon atmosphere, was added powdered, anhydrous K$_2$CO$_3$ (0.8 g, 5 eq, 5.85 mmol), followed by 2-bromopropane (1.15 ml, 11.7 mmol). The reaction mixture was stirred at room temperature for 24 h, when DCM:ether:MeOH (55:40:5), indicated that the reaction had gone to completion. The solvent was evaporated in vacuo and the residue partitioned between EtOAc (100 ml) and water (100 ml). The aqueous phase was extracted with more EtOAc (2×50 ml) and the combined organic phase washed with brine (50 ml), dried (MgSO$_4$) and evaporated in vacuo. The residue was purified by silica gel flash column chromatography, eluted with CHCl$_3$:MeOH (98:2) to afford the title compound as a slightly yellow film (195 mg, 55%). $\delta_H$ (CDCl$_3$, 250 MHz) 1.52 (6 H, d, J 7.5, CH[CH$_3$]$_2$), 2.5 (3 H, s, CH$_3$), 4.76-4.6 (3 H, m, NHCH$_2$ and CHMe$_2$), 7.06 (1 H, d, J 2.5, ArH), 7.35 (1 H, s, br, NH), 7.56 (2H, s, br, ArH), 8.47 (1 H, s, br, ArH); $\delta_C$ (CDCl$_3$, 250 MHz) 157.6 (C), 156.32 (C), 156 (C), 148.47 (CH), 137.72 (CH), 136.08 (CH), 130.83 (C), 123.11 (CH), 118.2 (C), 47.38 (CH), 43.2 (CH$_2$), 23.99 (CH$_3$), 22.5 (2×CH$_3$); m/z 301.2 (M+H)

2R,3S-3-(9-isopropyl-6-((6-methylpyridin-3-yl)methylamino)-9H-purin-2-ylamino)pentan-2-ol [2]

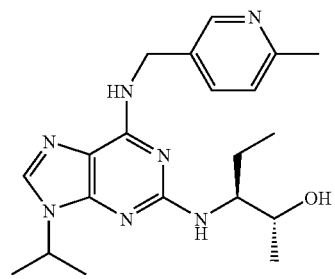 [SMILES: CC[C@H](Nc1nc(NCc2ccc(C)nc2)c2ncn(C(C)C)c2n1)[C@@H](C)O]

To a stirred solution of 2-fluoro-9-isopropyl-N-(6-methylpyridin-3-ylmethyl)-9-H-purin-6-amine (180 mg, 0.59 mmol) in n-BuOH/DMSO (5 ml, 4:1) at room temperature under an argon atmosphere was added DIEA (1 ml, 10 eq, 5.6 mmol) followed by (2R,3S)-3-amino-pentan-2-ol (0.34 g, 6 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a slight yellow oil (40 mg, 19%). $\delta_H$ (CDCl$_3$, 250 MHz) 0.95 (3 H, t, J 7.5, CHCH$_2$CH$_3$), 1.14 (3 H, d, J 5, CHCH$_3$OH), 154 (6 H, d, J 7.5, CH[CH$_3$]$_2$), 1.62-1.43 (2 H, m, CHCH$_2$CH$_3$), 2.44 (3 H, s, ArCH$_3$), 3.93 (1 H, m, CHMe$_2$), 4.77-4.58 (1 H, m, CHCH$_3$OH), 4.8-4.6 (2 H, m, NHCH$_2$Ar), 5.8 (1 H, s, br, NH), 6.82 (1 H, s, br, NH), 7.09 (1 H, d, J 10, ArH), 7.31-7.23 (2 H, m, ArH), 8.49 (1 H, s, br, ArH); $\delta_C$ (CDCl$_3$, 250 MHz) 157.71 (C), 156.28 (C), 155.95 (C), 148.58 (CH), 137.73 (CH), 129.01 (C), 128.52 (C), 128.42 (CH), 1231.14 (CH), 68.84 (CH), 50.45 (CH$_2$), 47.25 (CH), 23.27 (CH$_3$), 22.53 (2×CH$_3$), 20.9 (CH$_2$), 19.46 (CH$_3$), 10.45 (CH$_3$); m/z 384.3 (M+H)

Example 3

(3-Chlorobenzyl)-(2-fluoro-9H-purin-6-yl)amine

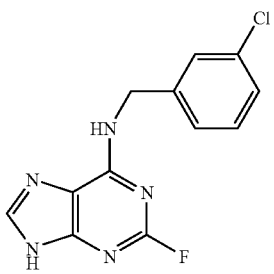 [SMILES: Fc1nc(NCc2cccc(Cl)c2)c2nc[nH]c2n1]

To a stirred solution of 6-chloro-2-fluoropurine (1 g, 1 eq, 5.9 mmol) in n-BuOH (50 ml) under an argon atmosphere, was added DIEA (2.6 ml, 2.5 eq, 14.75 mmol) followed by 3-chloro-benzylamine (1.25 g 1.5 eq, 8.85 mmol). The reaction mixture was heated at 100° C. for 3 hours after which the reaction was complete. The solvent was evaporated in vacuo and the residue purified by gradient column chromatography on silica gel, eluted with DCM:ether:MeOH (55:45:0→55:43:2), to afford the title compound as a white solid; Yield: 1.15 g (70%). $\delta_H$ (250 MHz, d$_6$-DMSO) 4.78-4.6 (2 H, m, NHCH$_2$Ar), 7.41-7.28 (4 H, m, ArH), 7.57 (1 H, s, br, ArH), 8.15 (1 H, s, br, NH), 8.88 (1 H, s, br, NH); $\delta_C$ (250 MHz, d$_6$-DMSO) 142.3 (C), 133.02 (C), 132.92 (C), 130.25 (CH), 130.17 (C), 127.82 (CH), 127.27 (CH), 127.03 (CH), 126.76 (C), 125.92 (CH), 116.4 (C), 115 (C), 42.67 (CH$_2$); m/z 278 (M+H)

(3-Chlorobenzyl)-(2-fluoro-9-isopropyl-9H-purin-6-yl)amine

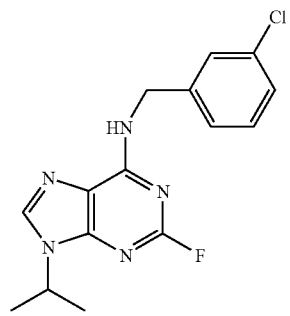 [SMILES: CC(C)n1cnc2c(NCc3cccc(Cl)c3)nc(F)nc21]

To a stirred solution of (3-chloro-benzyl)-(2-fluoro-9H-purin-6-yl)-amine (0.6 g, 2.16 mmol) in dimethylformamide (10 ml) at room temperature under an argon atmosphere, was added powdered, anhydrous potassium carbonate (1.47 g, 5 eq, 10.8 mmol), followed by 2-bromopropane (2.2 ml, 10 eq, 21.6 mmol). The reaction mixture was stirred at room temperature for 24 h, when DCM:ether:MeOH (55:40:5), indicated that the reaction had gone to completion. The solvent was evaporated in vacuo and the residue partitioned between ethyl acetate (50 ml) and water (50 ml). The aqueous phase was extracted with more ethyl acetate (2×50 ml) and the combined organic phase washed with brine (50 ml), dried (MgSO$_4$) and evaporated in vacuo. The residue was purified by silica gel flash column chromatography, eluted with CHCl$_3$ to afford the title compound as a slightly yellow gum; Yield: 0.45 g (65%). $\delta_H$ (250 MHz, CDCl$_3$) 1.57 (6H, d, J 7.5, CH[CH$_3$]$_2$), 4.81-4.63 (3 H, m, NHCH$_2$Ar and CHMe$_2$), 5.98 (1 H, s, br, NH), 7.29-7.19 (3 H, m, ArH), 7.34 (1 H, s, br, ArH), 7.42 (1 H, d, J 7.5, ArH), 7.51 (1 H, s, br, NH); $\delta_C$ (250 MHz, CDCl$_3$) 161.93 (C), 156.37 (C), 156.05 (C), 141.33 (C), 140.42 (C), 137.75 (CH), 134.49 (C), 129.92 (CH), 127.69 (CH), 125.81 (CH), 125.64 (CH), 47.43 (CH), 43.82 (CH$_2$), 22.56 (2×CH$_3$); m/z 320.3 (M+H)

2R,3S-3-(6-(3-Chlorobenzylamino)-9-isopropyl-9H-purin-2-ylamino)pentan-2-ol [3]

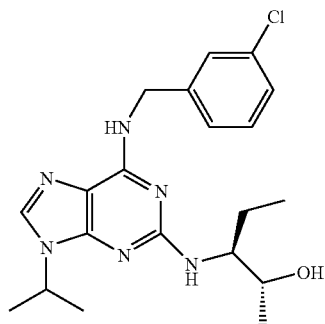

To a stirred solution of (3-chloro-benzyl)-(2-fluoro-9-isopropyl-9H-purin-6-yl)-amine (0.3 g, 0.93 mmol) in n-BuOH/

DMSO (5 ml, 4:1) at room temperature under an argon atmosphere was added DIEA (0.6 ml, 10 eq, 10 mmol) followed by (2R,3S)-3-amino-pentan-2-ol (0.5 g, 4.8 mmol). The reaction mixture was placed in a preheated oil bath at 140° C. and stirred at this temperature for 72 h, when TLC chloroform:methanol (95:5) indicated that the reaction had gone to completion. The reaction mixture was allowed to cool to room temperature and the solvent was evaporated in vacuo. The residue was partitioned between dichloromethane (100 ml) and water (100 ml), the aqueous phase was extracted with more dichloromethane (3×50 ml), and the combined organic phase was washed with brine (50 ml), dried (MgSO$_4$) and evaporated in vacuo. The residue was purified by gradient flash column chromatography on silica gel eluted with DCM:ether:MeOH (60:40:0→60:40:2) to afford the title product as a colorless film; Yield: 90 mg (22.5%). $\delta_H$ (250 MHz, CDCl$_3$) 0.97 (3 H, t, J 7.5, CHCH$_2$CH$_3$), 1.08 (3 H, d, J 7.5, CHCH$_3$OH), 1.45 (6 H, d, J 7.5, $\overline{CH}$[CH$_3$]$_2$), 1.6-1.35 (2 H, m, $\overline{CH}$CH$_2$CH$_3$), 3.93-3.8 (2 H, m, CHEt and NH), 4.55-4.45 [1 H, m, $\overline{CH}$(CH$_3$)OH], 4.74-4.64 ($\overline{3}$H, m, NHCH$_2$Ar and CHMe$_2$), 5.5 (1 H, s, br, OH), 6.53 (1H, s, br, NH), 7.19-7.13 (3 $\overline{H}$, m, ArH), 7.22 (1 H, s, ArH), 7.32 (1 H, s, ArH); $\delta_C$ (250 MHz, CDCl$_3$) 175.06 (C), 160.17 (C), 154.75 (C), 141.22 (C), 134.57 (CH), 134.29 (C), 129.73 (CH), 127.75 (CH), 127.30 (CH), 125.7 (CH), 114.56 (C), 71.53 (CH), 59.58 (CH), 46.44 (CH), 43.78 (CH$_2$), 23.96 (2×CH$_3$), 18.65 (CH$_3$), 18.32 (CH$_3$), 12.56 (CH$_3$); m/z 403.2 (M+H)

Example 4

3-Fluorobenzyl-2-fluoro-9H-purin-6-yl)amine

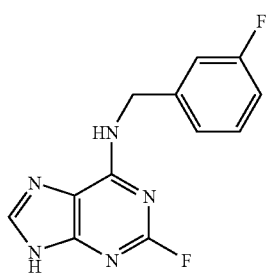 [SMILES: Fc1cccc(CNc2nc(F)nc3[nH]cnc23)c1]

To a stirred solution of 6-chloro-2-fluoropurine (1 g, 5.9 mmol) in n-BuOH (30 mL) under an argon atmosphere, was added DIEA (2.6 mL, 2.5 eq, 14.75 mmol) followed by 3-fluoro-benzylamine (1.1 g 1.5 eq, 8.85 mmol). The reaction mixture was heated at 100° C. for 3 hours after which the reaction was complete. The solvent was evaporated in vacuo and the residue purified by gradient flash column chromatography on silica gel, eluted with DCM:ether:MeOH (55:45:0→55:43:2), to afford the title compound as a white solid; Yield: 1.1 g (71.7%). $\delta_H$ (250 MHz, d$_6$-DMSO) 4.79-4.66 (2 H, s, br, NHCH$_2$Ar), 7.41-7.28 (4 H, m, ArH), 7.57 (1 H, s, br, ArH), 8.15 (1$\overline{H}$, s, br, NH), 8.87 (1 H, s, br, NH); $\delta_C$ (250 MHz, d$_6$-DMSO) 142.5 (C), 133.02 (C), 132.92 (C), 130.24 (CH), 130.17 (C), 128.41 (CH), 127.75 (C), 127.04 (CH), 126.76 (CH), 125.92 (CH), 116.2 (C), 115 (C), 42.68 (CH$_2$); m/z 262.1 (M+H)

3-Fluorobenzyl-(2-fluoro-9-isopropyl-9H-purin-6-yl)amine

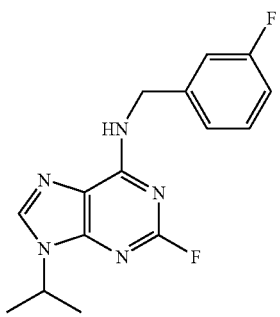 [SMILES: CC(C)n1cnc2c(NCc3cccc(F)c3)nc(F)nc21]

To a stirred solution of (3-fluoro-benzyl)-(2-fluoro-9H-purin-6-yl)-amine (0.6 g, 2.24 mmol) in dimethylformamide (10 ml) at room temperature under an argon atmosphere, was added powdered, anhydrous potassium carbonate (1.52 g, 5 eq, 11.2 mmol), followed by 2-bromopropane (2.3 ml, 10 eq, 22.4 mmol). The reaction mixture was stirred at room temperature for 24 h, when DCM:ether:MeOH (55:40:5), indicated that the reaction had gone to completion. The solvent was evaporated in vacuo and the residue partitioned between ethyl acetate (100 ml) and water (100 ml). The aqueous phase was extracted with more ethyl acetate (2×50 ml) and the combined organic phase washed with brine (50 ml), dried (MgSO$_4$) and evaporated in vacuo. The residue was purified by flash silica gel column chromatography, eluted with chloroform to afford the title compound as a slightly yellow gum; Yield: 0.37 g (54%). $\delta_H$ (250 MHz, CDCl$_3$) 1.55 (6 H, d, J 7.5, CH[CH$_3$]$_2$), 4.85-4.65 (3 H, m, NHCH$_2$Ar and CHMe$_2$), 5.96 (1 H, s, br, NH), 7.31-6.94 (4 H, m, $\overline{Ar}$H), 7.59 (1 H, s, br, ArH); $\delta_C$ (250 MHz, CDCl$_3$) 164.93 (C), 161.01 (C), 156.04 (C), 139.77 (C), 137.76 (CH), 130.13 (CH), 129.92 (C), 123.19 (CH), 114.59 (CH), 114.26 (CH), 47.22 (CH), 43.93 (CH$_2$), 22.56 (2×CH$_3$); m/z 304.2 (M+H)

2R,3S-3-[6-(3-Fluorobenzylamino)-9-isopropyl-9H-purin-2-ylamino]-pentan-2-ol [4]

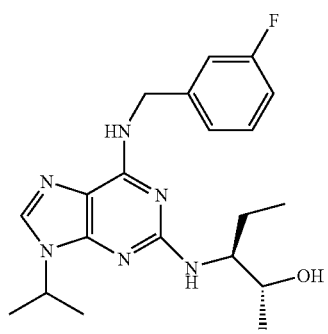 [SMILES: CC[C@H](Nc1nc(NCc2cccc(F)c2)c2ncn(C(C)C)c2n1)[C@@H](C)O]

To a stirred solution of (3-fluoro-benzyl)-(2-fluoro-9-isopropyl-9H-purin-6-yl)-amine (0.3 g, 0.99 mmol) in n-BuOH/DMSO (5 ml, 4:1) at room temperature under an argon atmosphere was added DIEA (0.6 ml, 10 eq, 10 mmol) followed by (2R,3S)-3-amino-pentan-2-ol (0.5 g, 4.8 mmol). The reaction mixture was placed in a preheated oil bath at 140° C. and stirred at this temperature for 72 h, when TLC chloroform: methanol (95:5) indicated that the reaction had gone to completion. The reaction mixture was allowed to cool to room temperature and the solvent was evaporated in vacuo. The residue was partitioned between dichloromethane (100 mL) and water (200 mL), the aqueous phase was extracted with more dichloromethane (3×50 mL), and the combined organic phase was washed with brine (50 mL), dried (MgSO$_4$) and evaporated in vacuo. The residue was purified by gradient flash column chromatography on silica gel eluted with DCM:ether:MeOH (60:40:0→60:40:2) to afford the title product as a colorless film; Yield: 80 mg (20%). δ$_H$(250 MHz, CDCl$_3$) 1.05 (3 H, t, J 7.5, CHCH$_2$CH$_3$), 1.15 (3 H, d, J 7.5, CHCH$_3$OH), 1.55 (6 H, d, J 7.5, CH[CH$_3$]$_2$), 1.65-1.4 (2 H, m, CHCH$_2$CH$_3$), 4-3.91 (2 H, m, CHEt and CHMe$_2$), 4.66-4.55 (1 H, m, CHMeOH), 4.8 (2 H, d, J 5, NHCH$_2$Ar), 6.41 (1 H, s, br, NH), 7.33-6.92 (4 H, m, ArH), 7.46 (1 H, s, br, ArH); δ$_C$ (250 MHz, CDCl$_3$) 165.2 (C), 164.92 (C), 160.18 (C), 154.77 (C), 141.67 (C), 141.56 (C), 134.59 (CH), 130.08 (CH), 123.14 (CH), 114.71 (CH), 113.95 (CH), 71.61 (CH), 59.65 (CH), 46.48 (CH), 43.94 (CH$_2$), 25.02 (CH$_2$), 22.52 (2×CH$_3$), 17.24 (CH$_3$), 10.59 (CH$_3$); m/z 387.3 (M+H)

Example 5

(9-Cyclopropylmethyl-2-fluoro-9H-purin-6-yl)-pyridin-3-ylmethyl-amine

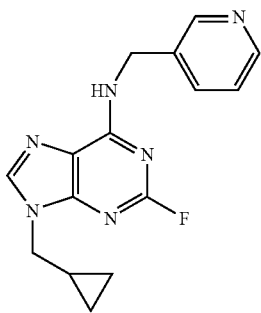 [SMILES: Fc1nc(NCc2cccnc2)c2ncn(CC3CC3)c2n1]

To a stirred solution of 2-fluoro-6-[(pyridin-3-ylmethyl)-amino]purine (1 g, 4.10 mmol) in DMF (12 ml) under argon atmosphere, at RT, was added K$_2$CO$_3$ (powdered, anhydrous, 2.84 g, 5 eq, 20.52 mmol) followed by (bromomethyl)cyclopropane (5.53 g 10 eq, 41 mmol). The reaction mixture was stirred at RT for 24 h, when TLC (CHCl$_3$: MeOH; 90:10) indicated that the reaction had gone to completion. The solvent was evaporated in vacuo and the residue partitioned between water (50 ml) and EtOAc (50 mL); the aqueous phase was separated and extracted with more EtOAc (2×50 ml). The bulked organic phase was washed with brine (50 ml), dried (MgSO$_4$) and evaporated in vacuo, and the residue was purified by gradient flash column chormoatography on silica gel, eluted with CHCl$_3$:MeOH (100:0→95:5), to afford the product as a colorless gum; Yield 0.8 g (68%) δ$_H$ (250 MHz, CDCl$_3$) 0.24-0.15 (2 H, m, CHH and CHH of Cp), 0.48-0.38 (2 H, m, CHH and CHH of Cp), 1.11-0.95 (1 H, m, CH of Cp), 2.56 (1 H, s, br, NH), 3.69 (2 H, d, J 7.5, HCH$_2$Cp), 4.58 (2 H, s, br, HCH$_2$Ar), 7.04-6.96 (1 H, m, ArH), 7.51-7.45 (2 H, m, ArH), 8.26-8.24 (1 H, m, ArH), 8.37 (1 H, s, br, ArH); δ$_C$ (250 MHz, CDCl$_3$) 156.32 (C), 156.01 (C), 149.29 (CH), 148.97 (CH), 139.85 (CH), 139.8 (C), 135.54 (CH), 133.81 (C), 123.51 (CH, 117.86 (C), 48.52 (CH$_2$), 42.09 (CH$_2$), 11.06 (CH$_3$), 5.28 (2×(CH$_2$); m/z 299.2 (M+H).

2R,3S-3-(9-(Cyclopropylmethyl)-6-(pyridin-3-ylmethylamino)-9H-purin-2-ylamino)pentan-2-ol [5]

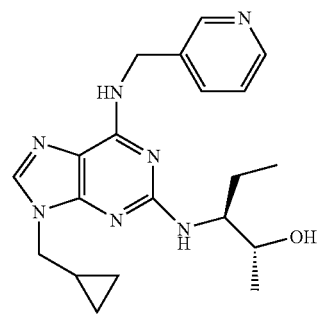 [SMILES: CC[C@H](Nc1nc(NCc2cccnc2)c2ncn(CC3CC3)c2n1)[C@@H](C)O]

To a stirred solution of (9-cycloproylmethyl-2-fluoro-9H-purin-6-yl)-pyridin-3-ylmethyl-amine (300 mg, 1 mmol) in n-BuOH/DMSO (5 ml, 4:1) at room temperature under an argon atmosphere was added DIEA (1.9 mL, 10 eq, 10.5 mmol) followed by (2R,3S)-3-amino-pentan-2-ol (500 mg, 4.8 eq, 4.8 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between ethyl acetate (50 ml) and water (50 ml), the aqueous phase was extracted with more ethyl acetate (2×25 ml), and the combined organic phase was washed with brine (50 ml), dried (MgSO$_4$) and evaporated in vacuo. The residue was purified by flash gradient column chromatography on silica gel eluted with CHCl$_3$:MeOH (100:0→95:5), to afford the product as a colorless film. Yield (85 mg, 22%). δ$_H$ (250 MHz, CDCl$_3$) 0.45-0.35 (2 H, m, CHH and CHH of Cp), 0.7-0.6 (2 H, m, CHH and CHH of Cp), 1.02 (3 H, t, J 7.5, CHCH$_2$CH$_3$), 1.16 (3 H, d, J 7.5, CHCH$_3$OH), 1.35-1.2 (1 H, m, CHCH HCH$_3$), 1.68-1.38 (2 H, m, CHCHHCH$_3$ and CH of Cp), 3.9-3.8 (2 H, m, CHOH and CHEt), 4.05 (2 H, d, J 7.5, NC H$_2$Cp), 4.76 (2 H, s, br, NHCH$_2$Ar), 4.87 (1 H, d, J 5, OH), 5.77 (1 H, s, br, NH), 6.67 (1 H, s, br, NH), 7.22-7.17 (1 H, m, ArH), 7.53 (1 H, s, ArH), 7.65 (1 H, dd, J 2.5, 7.5, ArH), 8.5 (1H, d, J 5, ArH), 8.61 (1H, s, ArH) 1.11-0.95 (1 H, m, CH of Cp), 2.56 (1 H, s, br, NH), 3.69 (2 H, d, J 7.5, NCH$_2$Cp), 4.58 (2 H, s, br, NHCH$_2$Ar), 7.04-6.96 (1 H, m, ArH), 7.51-7.45 (2 H, m, ArH), 8.26-8.24 (1 H, m, ArH), 8.37 (1 H, s, br, ArH); δ$_C$ (250 MHz, CDCl$_3$) 160.3 (C), 154.71 (C), 151.05 (C), 151.05 (C), 149.28 (CH), 148.64 (CH), 136.85 (CH), 135.30 (CH), 134.56 (C), 129.2 (C), 123.37 (CH), 122.1 (C), 114.21 (C), 77.27 (CH), 59.5 (CH), 48.02 (CH$_2$), 41.99 (CH$_2$), 24.84 (CH$_2$), 17.4 (CH$_3$), 11.53 (CH$_3$), 11.01 (CH$_3$), 4.2 (CH$_2$); m/z 382.3 (M+H)

Example 6

6-Chloro-2-fluoro-9-isopropyl-9H-purine

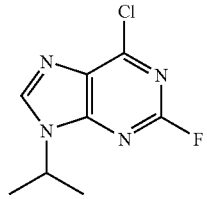

A mixture of 2-fluoro,6-chloro-purine (2 g, 11.7 mmol), and powdered potassium carbonate (4 g, 28 mmol) was vigorously stirred in 30 ml DMF. Isopropyliodide (6 ml, 60 mmol) was added very slowly over 2 h. The reaction was stirred for a further 5 h. DMF was removed and the crude taken up in ethyl acetate, washed with water (50 ml), brine (50 ml), dried (MgSO$_4$) and concentrated. The crude was purified by silica gel column chromatography (30% ethyl acetate in hexane) to provide the pure product as a white solid (1.1 g, 44%). δ$_H$ (CD$_3$OD, 250 MHz) 1.65 [6 H, d, J 7.5, CH(CH$_3$)$_2$], 4.92 [1 H, m, CH(CH$_3$)$_2$], 8.66 (1 H, s, ArH); δ$_C$ (CD$_3$OD, 250 MHz) 154.7 (C), 153.88 (C), 152.2 (C), 147.65 (CH), 132.44 (C), 50.66 (CH), 22.72 (2×CH$_3$); m/z 215.2 (M+H)

N-Cyclopropyl-2-fluoro-9-isopropyl-9H-purin-6-amine

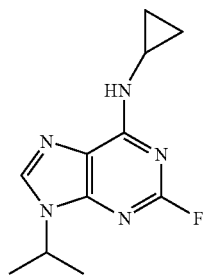 [SMILES: CC(C)n1cnc2c(NC3CC3)nc(F)nc21]

6-Chloro-2-fluoro-9-isopropyl-9H-purine (0.3 g, 1.4 mmol), diisopropylethylamine (0.2 g, 1.55 mmol) and cyclopropylamine (0.2 g, 2.66 mmol) were stirred together in ethanol (30 ml) at room temperature for 6 h. Volatiles were removed and the residue taken up in ethyl acetate, washed with water (50 ml), brine (50 ml), dried (MgSO$_4$) and concentrated. The crude was purified by silica gel flash column chromatography (ethyl acetate:hexane 3:2) to give the pure product (232 mg, 70.5%) δ$_H$ (CDCl$_3$, 500 MHz) 0.63-0.55 (2 H, m, CHHCHH of Cp), 0.85-0.78 (2 H, m, CHHCHH of Cp), 1.54 (6H, d, J 7.5, CH[CH$_3$]$_2$), 2.97 (1 H, s, br, CH of Cp), 4.73-4.62 (1 H, m, CHMe$_2$), 6.72 (1 H, s, br, NH) 7.7 (1 H, s, ArH); δ$_C$ (CDCl$_3$, 500 MHz) 159.29 (C), 157.63 (C), 156.8 (C), 156.64 (C), 137.69 (CH), 47.35 (CH), 22.6 (2×CH$_3$), 21.06 (CH), 7.28 (2×CH$_2$); m/z 236.2 (M+H)

2R,3S-3-(6-Cyclopropylamino)-9-isopropyl-9H-purin-2-ylamino)pentan-2-ol [6]

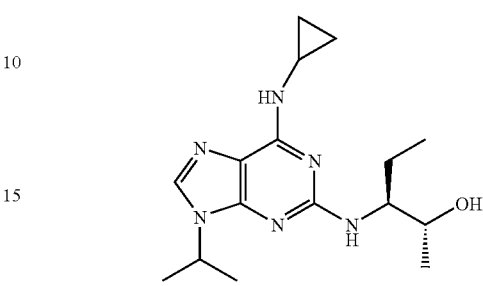

To a stirred solution of N-cyclopropyl-2-fluoro-9-isopropyl-9H-purin-6-amine (232 mg, 0.99 mmol) in N-methylpyrrolidinone (10 ml) at room temperature under an argon atmosphere was added DIEA (0.2 mL, 10.96 eq, 1.14 mmol) followed by (2R,3S)-3-aminopentan-2-ol (540 mg, 5 eq, 5.25 mmol). The reaction mixture was placed in a preheated oil bath at 140° C. and stirred at this temperature for 24 h. The reaction mixture was allowed to cool to room temperature and excess water was added whereupon the product oiled out. Added ethyl acetate and washed the organic layer carefully with water (3×50 ml), dried (MgSO$_4$) and evaporated in vacuo. The residue was purified by flash column chromatography on silica gel eluted with ethyl acetate to afford the title product as a pale brown solid (46 mg, 15%). δ$_H$ (CDCl$_3$, 500 MHz) 0.58-0.49 (2 H, m, CHHCHH of Cp), 0.83-0.81 (2 H, m, CHHCHH of Cp), 1.03 (3H, t, J 7.5, CHCH$_2$CH$_3$), 1.13 (3 H, d, J 7.5, CHCH$_3$OH), 1.55 (6 H, d, J 7.5, CH[CH$_3$]$_2$), 1.57-1.45 (2 H, m, CHCH$_2$CH$_3$), 2.91 (1H, s, b, CH of Cp), 3.95 (2 H, s, br, CHMe$_2$ and CHEt), 4.6-4.57 (1 H, m, CHMeOH), 4.84 (1 H, s, br, NH), 6.25 (1H, s, br, NH), 7.49 (1 H, s, ArH); δ$_C$ (CDCl$_3$, 500 MHz) 160.16 (C), 155.91 (C), 150.24 (C), 134.57 (CH), 114.63 (C), 71.57 (CH), 59.88 (CH), 46.27 (CH), 25.15 (CH$_2$), 22.59 (CH$_3$), 17.22 (CH$_3$), 11.61 (CH$_3$), 7.34 (CH$_2$). 47.35 (CH), 22.6 (2×CH$_3$), 21.06 (CH), 7.28 (2×CH$_2$); m/z 319.3 (M+H)

Example 7

N-(Cyclopropylmethyl)-2-fluoro-9-isopropyl-9H-purine-6-amine

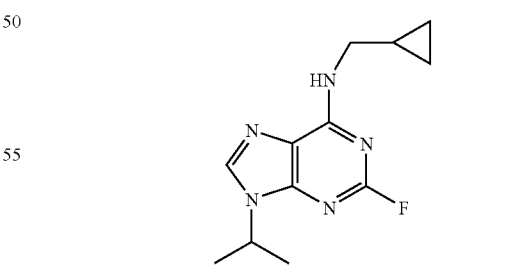

6-Chloro-2-fluoro-9-isopropyl-9H-purine (0.3 g, 1.4 mmol), diisopropylethylamine (0.2 g, 1.55 mmol) and cyclopropylmethylamine (0.24 g, 2.7 mmol) were stirred together in ethanol (30 ml) at room temperature for 6 h. Volatiles were removed and the residue taken up in ethyl acetate, washed with water (50 ml), brine (50 ml), dried (MgSO$_4$) and concentrated. The crude was purified by silica gel flash column chromatography (ethyl acetate:hexane 3:2) to give the pure product (290 mg, 83%) as a colorless gum. δ$_H$ (CDCl$_3$, 500 MHz) 0.29-0.27 (2 H, m, CHHCHH of Cp), 0.56-0.54 (2H, m, CHHCHH of Cp), 1.13 (1H, s, br, CH of Cp), 1.58 (6 H, d, J 7.5, CH[CH$_3$]$_2$), 3.44 (2 H, s, br, NHCH$_2$Cp) 2.97 (1 H, s, br, CH of Cp), 4.74-4.72 (1 H, m, CHMe$_2$), 6.22 (1 H, s, br, NH), 7.76 (1 H, s, ArH); δ$_C$ (CDCl$_3$, 500 MHz) 160.09 (C), 156.14 (C), 147.4 (C), 137.38 (CH), 118.26 (C), 47.14 (CH), 45.78 (CH$_2$), 22.46 (2×CH$_3$), 10.06 (CH), 3.5 (2×CH$_2$)

2R,3S-3-(6-(Cyclopropylmethylamino)-9-isopropyl-9H-purine-2-ylamino)pentan-2-ol [7]

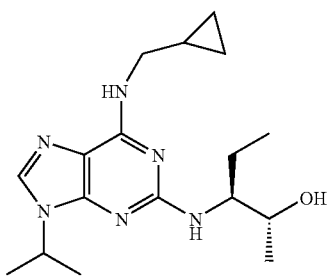 [SMILES: CC[C@H](Nc1nc(NCC2CC2)c2ncn(C(C)C)c2n1)[C@@H](C)O]

To a stirred solution of N-(cyclopropylmethyl)-2-fluoro-9-isopropyl-9H-purin-6-amine (290 mg, 1.1 mmol) in N-methylpyrrolidinone (10 ml) at room temperature under an argon atmosphere was added DIEA (1.42 g, 11.1 mmol) followed by (2R,3S)-3-a minopentan-2-ol (566 mg, 5 eq, 5.5 mmol). The reaction mixture was placed in a preheated oil bath at 140° C. and stirred at this temperature for 24 h. The reaction mixture was allowed to cool to room temperature and excess water was added whereupon the product oiled out. Added ethyl acetate and washed the organic layer carefully with water (4×, 50 ml). The organic phase was washed with brine (50 mL), dried (MgSO$_4$) and evaporated in vacuo. The residue was purified by flash column chromatography on silica gel eluted with ethyl acetate to afford the title product as a pale brown solid (120 mg, 31%); δ$_H$ (CDCl$_3$, 500 MHz) 0.22-0.19 (2 H, m, CHHCHH of Cp), 0.36-0.34 (2H, m, CHHCHH of Cp), 0.8 (3H, t, J 7.5, CHCH$_2$CH$_3$), 0.89 (3 H, d, J 7.5, CHC H$_3$OH) 1.13 (1H, s, br, CH of Cp), 1.33 (6H, d, J 7.5, CH[C H$_3$]$_2$), 3.24 (2 H, s, br, NHCH$_2$Cp), 3.7 (2 H, s, br, CHEt and CHMe$_2$), 6.52 (1 H, s, br, NH), 7.26 (1 H, s, ArH); δ$_C$ (CDCl$_3$, 500 MHz) 160.2 (C), 154.89 (C), 134.35 (CH), 71.72 (CH), 59.76 (CH), 46.238 (CH), 25.23 (CH$_2$), 22.59 (CH$_3$), 17.15 (CH$_3$), 11.61 (CH$_3$), 3.48 (2×CH$_2$); m/z 333.3 (M+H)

Example 8

N-Cyclobutyl-2-fluoro-9-isopropyl-9H-purin-6-amine

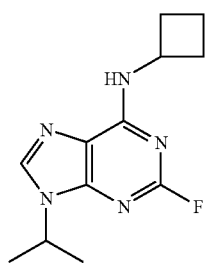 [SMILES: CC(C)n1cnc2c(NC3CCC3)nc(F)nc21]

6-chloro-2-fluoro-9-isopropyl-9H-purine (0.3 g, 1.4 mmol), diisopropylethylamine (0.2 g, 1.55 mmol) and cyclobutylamine (0.2 g, 2.8 mmol) were stirred together in ethanol (30 ml) at room temperature for 6 h. Volatiles were removed and the residue taken up in ethyl acetate, washed with water (50 ml), brine (50 ml), dried (MgSO$_4$) and concentrated. The crude was purified by silica gel flash column chromatography (ethyl acetate:hexane 3:2) to give the pure product (237 mg, 68%) δ$_H$ (CDCl$_3$, 500 MHz) 1.56 (6H, d, J 7.5, CH[CH$_3$]$_2$), 1.76-1.74 (2 H, m, CH$_2$ of Cyclobutyl), 1.98-1.94 (2 H, m, CH$_2$ of cyclobutyl), 2.45 (2 H, s, br, CH$_2$ of cyclobutyl)) 4.72-4.7 (2 H, m, CH of cyclobutyl and CHMe$_2$), 6.35 (1 H, s, br, NH), 7.75 (1 H, s, ArH); δ$_C$ (CDCl$_3$, 500 MHz) 160.08 (C), 158.43 (C), 155.34 (C), 155.18 (C), 150.09 (C), 137.44 (CH), 47.26 (CH), 31.56 (2×CH$_2$), 22.38 (2×CH$_3$), 15.09 (CH$_2$); m/z 250.2 (M+H)

2R,3S-3-(6-(Cyclobutylamino)-9-isopropyl-9H-purin-2-ylamino)pentan-2-ol [8]

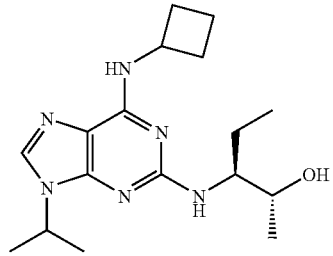 [SMILES: CC[C@H](Nc1nc(NC2CCC2)c2ncn(C(C)C)c2n1)[C@@H](C)O]

To a stirred solution of N-cyclobutyl-2-fluoro-9-isopropyl-9H-purin-6-amine (237 mg, 0.95 mmol) in N-methylpyrrolidinone (10 ml) at room temperature under an argon atmosphere was added DIEA (1.28 g, 10 mmol) followed by (2R,3S)-3-aminopentan-2-ol (566 mg, 5 eq, 5.5 mmol). The reaction mixture was placed in a preheated oil bath at 140° C. and stirred at this temperature for 24 h. The reaction mixture was allowed to cool to room temperature and excess water was added whereupon the product oiled out. Added ethyl acetate and washed the organic layer carefully with water (4×50 ml). The organic phase was washed with brine (50 ml), dried (MgSO$_4$) and evaporated in vacuo. The residue was purified by flash column chromatography on silica gel eluted with ethyl acetate to afford the title product as a pale brown solid (120 mg, 31%); δ$_H$ (CDCl$_3$, 500 MHz), 0.97 (3 H, t, J 7.5, CHCH$_2$CH$_3$), 1.07 (3 H, d, J 7.5, CHCH$_3$OH), 1.47 (6 H, d, J 7.5, CH[CH$_3$]$_2$), 1.53-1.42 (2 H, m, CHCH$_2$CH$_3$), 1.71-1.68 (2H, m, CH$_2$ of cyclobutyl), 1.89-1.87 (2H, m, CH$_2$ of cyclobutyl), 2.39-2.37 (2H, m, CH$_2$ of cyclobutyl), 3.89 (1 H, d, J 5, NHcyclobutyl)), 4.53-4.5 (3 H, m, CHMe$_2$ and CHEt and CH of cyclobutyl), 5.62 (1 H, m, CHMeOH), 6.15 (1H, s, br, NH), 7.43 (1 H, s, ArH); δ$_C$ (CDCl$_3$, 500 MHz) 161.16 (C), 154.76 (C), 152.2 (C), 134.43 (CH), 114.67 (C), 71.7 (CH), 59.74 (CH), 46.36 (CH), 31.68 (CH$_2$), 25.25 (2×CH$_2$), 22.59 (CH$_3$), 17.11 (CH$_3$), 15.04 (CH$_2$), 11.61 (CH$_3$); m/z 333.3 (M+H)

Example 9

(2-Fluoro-9H-purin-6-yl)-pyridin-4-ylmethylamine

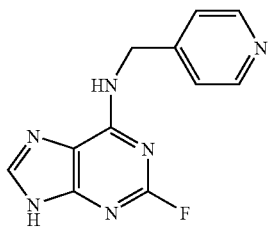 [SMILES: Fc1nc(NCc2ccncc2)c2nc[nH]c2n1]

To a stirred solution of 6-chloro-2-fluoropurine (1 g, 5.8 mmol) in n-BuOH (50 mL) under an argon atmosphere at 0° C., was added diisopropylethylamine (3 ml, 17.4 mmol) followed by 4-(aminomethyl)pyridine (0.9 ml, 1.5 eq, 8.7 mmol). The reaction mixture was stirred at this temperature for 1 h and then allowed to return to room temperature and stirred for 4 h, when TLC(CHCl$_3$:MeOH; 90:10) indicated that the reaction had gone to completion. The solvent was evaporated in vacuo and the residue was purified by gradient flash column chromatography on silica gel, eluted with CHCl$_3$:MeOH (100:0→90:10), to afford the product as a white solid; Yield: 0.85 g (60%). mp 200-202° C. $^1$H-NMR (d$_6$-DMSO, 250 MHz): δ 4.67 (2 H, d, J 5, —HNC$\underline{H_2}$-Pyr), 7.34-7.28 (2 H, m, Pyr-H), 8.48-8.42 (2 H, m, Pyr-$\overline{H}$), 8.54 (1 H, s, —N=C$\overline{H}$—NH—), 8.84 (1 H, s, br, —$\underline{H}$NCH$_2$-Pyr), 13.13 (1 H, s, b, —N=CH—$\overline{NH}$—); m/z 245 ([M+H]$^+$ (2-Fluoro-9-isopropyl-9H-purin-6-yl)pyridine-4-ylmethylamine

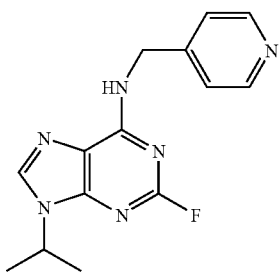 [SMILES: CC(C)n1cnc2c(NCc3ccncc3)nc(F)nc21]

To a stirred solution of (2-Fluoro-9H-purin-6-yl)-pyridin-4-ylmethyl-amine (0.6 g, 2.46 mmol) in DMF (10 mL) under an argon atmosphere, at RT, was added K$_2$CO$_3$ (powdered, anhydrous, 1.7 g, 5 eq, 12.3 mmol) followed by 2-bromopropane (2.3 ml, 10 eq, 24.6 mmol). The reaction mixture was stirred at RT for 24 h, when TLC (CHCl$_3$:MeOH; 90:10) indicated that the reaction had gone to completion. The solvent was evaporated in vacuo and the residue partitioned between water (200 ml) and EtOAc (50 ml). The aqueous phase was separated and extracted with more EtOAc (2×50 mL). The bulked organic phase was washed with brine (50 ml), dried (MgSO$_4$) and evaporated in vacuo, and the residue was purified by gradient column chromatography on silica gel, eluted with chloroform:methanol (100:0→95:5), to provide the product as a white solid; Yield: 0.40 g (57%). mp 170-173° C. $^1$H-NMR (d$_6$-DMSO, 250 MHz): δ 1.49 (6 H, d, J 7.5, —CH(CH$_3$)$_2$), 4.63 (3 H, m, —C$\underline{H}$(CH$_3$)$_2$+—HN C$\underline{H_2}$-Pyr), 7.30, 8.47 (4 H, 2×m, Pyr-H), 8.28 (s, 1 H, —N=$\overline{CH}$—N—), 8.97 (1 H, s, br, —$\underline{HN}$CH$_2$-Pyr). m/z: 287 ([M+$\overline{H}$].

2R,3S-3-(9-Isopropyl-6-(pyridine-4-ylmethylamino)-9H-purin-2-ylamino)pentan-2-ol [9]

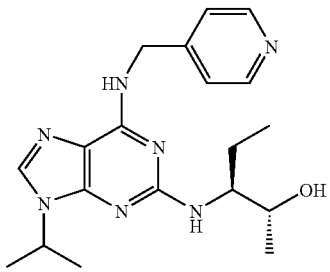 [SMILES: CC[C@H](Nc1nc(NCc2ccncc2)c2ncn(C(C)C)c2n1)[C@@H](C)O]

To a stirred solution of (2-fluoro-9-isopropyl-9H-purin-6-yl)-pyridin-4-ylmethyl-amine (300 mg, 1.05 mmol) in n-BuOH/DMSO (5 ml, 4:1) at room temperature under an argon atmosphere was added DIEA (2 ml, 10 eq, 10.5 mmol) followed by (2R,3S)-3-amino-pentan-2-ol (600 mg, 5.5 eq, 5.8 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the product as a colorless film. Yield (225 mg, 58%); δ$_H$ (CDCl$_3$, 500 MHz) 0.92 (3 H, t, J 7.5, CHCH$_2$C$\underline{H_3}$), 1.05 (3 H, d, J 7.5, CHC$\underline{H_3}$OH), 1.4 (6 H, d, J 7.5, C$\overline{H}$[CH$_3$]$_2$), 1.47-1.36 (2H, m, CHC H$_2$CH3), 3.88-3.85 (2 H, m, CHEt and NH), 4.53-4.5 (1 H, m, $\overline{CH}$CH$_3$OH), 4.72 (2H, s, br, N$\overline{H}$CH$_2$Ar), 6.5 (1 H, s, br, NH), 7.$\overline{2}$ (2 H, s, br, ArH), 7.45-7.42 (1 H, m, ArH), 8.46-8.43 (2 H, m, ArH); δ$_C$ (CDCl$_3$, 500 MHz) 154.66 (C), 149.86 (2×CH), 149.69 (C), 148.26 (C), 134.84 (CH), 122.22 (2×CH), 71.51 (CH), 59.57 (CH), 46.58 (CH), 43.45 (CH$_2$), 24.9 (CH$_2$), 22.59 (2×CH$_3$), 17.27 (CH$_3$), 11.53 (CH$_3$); m/z 370.2 (M+H)

Example 10

2,6-Dimethylisonicotinonitrile

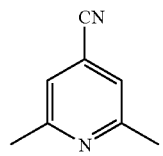

To a stirred quantity of 2,6-lutidine-1-oxide (12.3 g, 100 mmol) was slowly added dimethyl sulphate (12.6 g, 100 mmol) at such a rate that the temperature of the reaction mixture was maintained at 80° C. throughout the addition. When the addition was complete (about one hour) the solution was stirred at that temperature for an additional 2 h. The salt crystallised upon cooling and was recrystallised from anhydrous acetone giving white prisms; m.p 96-97° C. Yield 18 g (73%). To a solution of this 1-methoxy-2,6-dimethylpyridinium methyl sulphate (11.65 g, 50 mmol) dissolved in water (50 ml), under nitrogen, was added a solution of potassium cyanide (10 g, 150 mmol) dissolved in 50 ml of water. The solution was allowed to stand at room temperature for 2 days at which time the nitrile, which had separated from the solution as long white needles, was removed by filtration, yielding 2.8 g of pure product (42%) $\delta_H$ (CDCl$_3$, 500 MHz) 2.44 (6 H, s, 2×CH$_3$), 4.2 (2 H, d, J 5, NHCH$_2$), 6.78 (2 H, s, ArH); $\delta_C$ (CDCl$_3$, 500 MHz) 157.83 (2×C), 122.71 (C), 118.2 (2×CH), 24.28 (2×CH$_3$)

t-Butyl (2,6-dimethylpyridin-4-yl)methyl carbamate

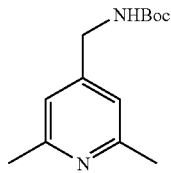

2,6-dimethylisonicotinonitrile (2 g, 15.15 mmol) was dissolved in 10% acetic acid/ethanol (30 ml). 10% palladium over charcoal catalyst (0.5 g) was added and the reaction stirred under an atmosphere of hydrogen for 24 h. at 60° C. The mixture was filtered through a pad of celite, Volatiles were removed and the crude residue dissolved in dichloromethane (30 ml). To the stirred solution was then added triethylamine (5 ml) followed by di-tert-butyldicarbonate (3.3 g, 15.15 mmol). After 3 h, the solvent was removed and the residue dissolved in ethyl acetate. It was washed with water (50 ml), saturated bicarbonate (50 ml), dried and evaporated. The crude product was purified by silica gel flash column chromatography (ethyl acetate:hexane 1:2) to provide 0.6 g of pure title compound (17.24% yield). $\delta_H$ (CDCl$_3$, 500 MHz) 1.42 (9 H, s, 3×CH$_3$), 2.44 (6 H, s, 2×CH$_3$), 4.2 (2 H, d, J 5, NHCH$_2$), 5.25 (1 H, s, b, NH), 6.81 (2 H, s, ArH); $\delta_C$ (CDCl$_3$, 500 MHz) 157.83 (C), 156.01 (CO), 148.71 (C), 118.58 (2×CH), 79.77 (C), 43.41 (CH$_2$), 28.34 (3×CH$_3$), 24.28 (2×CH$_3$); m/z 237.2 (M+H)

N-((2,6-Dimethylpyridin-4-yl)methyl)-2-fluoro-9H-purin-6-amine

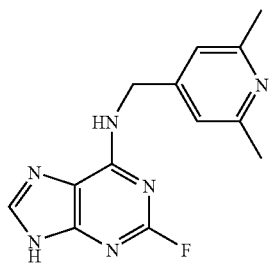 [SMILES: Cc1cc(CNc2nc(F)nc3[nH]cnc23)cc(C)n1]

To a stirred solution of 6-chloro-2-fluoropurine (0.4 g, 2.9 mmol) in n-BuOH (50 ml) under an argon atmosphere at 0° C., was added DIEA (2.5 ml, 14.7 mmol) followed by (2,6-dimethylpyridin-4-yl)methanamine (0.54 g, 4 mmol). The reaction mixture was stirred at this temperature for 1 h and then allowed to return to room temperature and stirred for 4 h, it was still seen incomplete, hence heated the reaction to 100° C. and left at that temperature for 8 h. The solvent was evaporated in vacuo and the residue was purified by gradient flash column chromatography on silica gel, eluted with CHCl$_3$:MeOH (100:0→90:10), to afford the product as a white solid; Yield: 0.5 g (63%); $\delta_H$ CDCl$_3$, 250 MHz) 2.48 (6H, s, 2×CH$_3$), 3.65-3.54 (2 H, m, NHCH$_2$), 4.61 (1 H, s, br, NH), 7.32 (2 H, s, ArH), 7.84 (1 H, s, ArH)), 9.05 (1 H, s, br, NH); $\delta_C$ (CDCl$_3$, 250 MHz) 159.2 (C), 156.62 (C), 156.61 (C), 155.46 (C), 146.92 (CH), 136.3 (C), 122.05 (2×CH), 119.48 (C), 41.6 (CH$_2$), 18.06 (2×CH$_3$)

N-((2,6-Dimethylpyridin-4-yl)methyl)-2-fluoro-9-isopropyl-9H-purin-6-amine

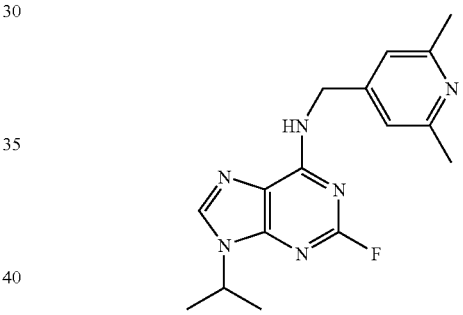

To a stirred solution of 2-fluoro-N-(2,6-methylpyridin-4-yl)methyl-9H-purin-6-amine (0.4 g, 1.48 mmol) in dimethylformamide (10 ml) at room temperature under an argon atmosphere, was added powdered, anhydrous K$_2$CO$_3$ (1 g, 5 eq, 7.4 mmol), followed by 2-bromopropane (1.2 ml, 12.2 mmol). The reaction mixture was stirred at room temperature for 24 h, when DCM:ether:MeOH (55:40:5), indicated that the reaction had gone to completion. The solvent was evaporated in vacuo and the residue partitioned between EtOAc (50 ml) and water (50 ml). The aqueous phase was extracted with more EtOAc (2×50 ml) and the combined organic phase washed with brine (50 ml), dried (MgSO$_4$) and evaporated in vacuo. The residue was purified by silica gel column chromatography, eluted with CHCl$_3$:MeOH (98:2) to afford the title compound as a colorless film (250 mg, 54%). $\delta_H$ (CDCl$_3$, 500 MHz) 1.46 (6H, d, J 7.5, CH[CH$_3$]$_2$), 2.38 (3 H, s, ArCH$_3$), 2.39 (3 H, s, ArCH$_3$), 4.73-4.6 (3 H, m, NHCH$_2$ and CHMe$_2$), 6.85 (1 H, s, ArH), 7.35 (1 H, s, br, NH), 7.5 (1 H, s, br, ArH); $\delta_C$ (CDCl$_3$, 500 MHz) 157.8 (C), 158.6 (C), 154.32 (C), 151 (C), 148.42 (CH), 122.2 (2×CH), 121.08 (C), 47.52 (CH), 43.6 (CH$_2$), 23.68 (2×CH$_3$), 22.3 (2×CH$_3$); m/z 315.2 (M+H)

2R,3S-3-(9-Isopropyl-6-(2,6-dimethylpyridine-4-ylmethylamino)-9H-purin-2-ylamino)pentan-2-ol [10]

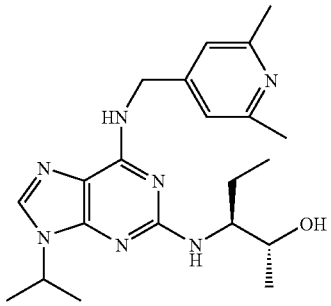 [SMILES: CC[C@H](Nc1nc(NCc2cc(C)nc(C)c2)c2ncn(C(C)C)c2n1)[C@@H](C)O]

To a stirred solution of 2-fluoro-9-isopropyl-N-(2,6-dimethylpyridin-4-ylmethyl)-9-H-purin-6-amine (250 mg, 0.8 mmol) in n-BuOH/DMSO (5 ml, 4:1) at room temperature under an argon atmosphere was added DIEA (1.4 ml, 10 eq, 8 mmol) followed by (2R,3S)-3-amino-pentan-2-ol (0.35 g, 3.4 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a colorless oil (56 mg, 18%). $\delta_H$ (CDCl$_3$, 500 MHz) 0.95 (3 H, t, J 7.5, CHCH$_2$CH$_3$), 1.05 (3 H, d, J 5, CHCH$_3$OH), 1.43 (6 H, d, J 10, CH[CH$_3$]$_2$), 1.55-1.4 (2 H, m, CHCH$_2$CH$_3$), 2.43 (3 H, s, ArCH$_3$), 2.44 (3 H, s, ArCH$_3$), 3.9-3.8 (2 H, m, CHEt and CHMe$_2$), 4.57-4.46 (1 H, m, CHCH$_3$OH), 4.63-4.58 (2 H, m, NHCH$_2$Ar), 6.28 (1H, s, br, NH), 6.8 (2 H, s, br, ArH), 7.45 (1 H, s, ArH); $\delta_C$ (CDCl$_3$, 250 MHz) 160.08 (C), 157.76 (C), 155.36 (C), 148.97 (C), 135.36 (C), 134.75 (CH), 118.95 (2×CH), 71.52 (CH), 59.59 (CH), 46.65 (CH), 44.92 (CH$_2$), 24.91 (CH$_2$), 24.01 (2×CH$_3$), 22.5 (2×CH$_3$), 17.27 (CH$_3$), 11.51 (CH$_3$); m/z 398.3 (M+H)

Example 11

2-Fluoro-N-((6-trifluoromethyl)pyridine-3-yl)methyl)-9H-purin-6-amine

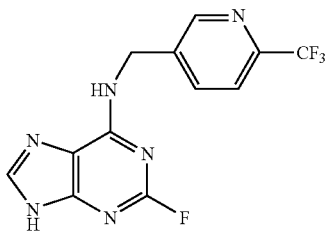 [SMILES: Fc1nc(NCc2ccc(C(F)(F)F)nc2)c2nc[nH]c2n1]

To a stirred solution of 6-chloro-2-fluoropurine (344 mg, 2 mmol) and [6-(trifluoromethyl)pyridine-3-yl]methanamine (0.4 g, 2.27 mmol) in n-BuOH (50 ml) under an argon atmosphere at 0° C., was added DIEA (2.5 ml, 14.7 mmol). The reaction mixture was stirred at this temperature for 1 h and then allowed to return to room temperature and stirred for 4 h, it was still seen incomplete, hence heated the reaction to 100° C. and left at that temperature for 5 h. The solvent was evaporated in vacuo and the residue was purified by gradient column chromatography on silica gel, eluted with CHCl$_3$:MeOH (100:0→90:10), to afford the product as a white solid; Yield: 0.46 g (75%) $\delta_H$ (CDCl$_3$, 500 MHz) 3.62-3.57 (2 H, m, NHCH$_2$), 4.69 (1 H, s, br, NH), 7.2-7.1 (2 H, s, br, ArH and NH), 7.69 (1 H, d, J, 7.5, ArH), 8.27 (1 H, s, ArH), 8.71 (1 H, s, ArH); $\delta_C$ (CDCl$_3$, 500 MHz) 158.69 (C), 158.18 (C), 157.67 (C), 154.56 (C), 147.48 (CH), 146.99 (CH), 144.32 (C), 133.87 (CH), 121.67 (CH), 118.88 (C), 43.48 (CH$_2$); m/z 313.1 (M+H)

2-Fluoro-9-isopropyl-N46-(trifluoromethyl)pyridine-3-yl)methyl)-9H-purin-6-amine

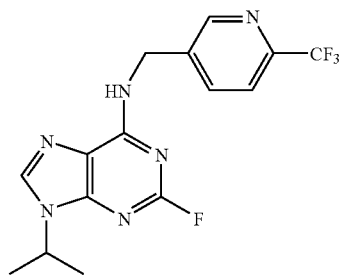 [SMILES: CC(C)n1cnc2c(NCc3ccc(C(F)(F)F)nc3)nc(F)nc21]

To a stirred solution of 2-fluoro-N-[(6-(trifluoromethyl)pyridin-3-yl)methyl-9H-purin-6-amine (0.4 g, 1.27 mmol) in dimethylformamide (10 ml) at room temperature under an argon atmosphere, was added powdered, anhydrous K$_2$CO$_3$ (0.86 g, 5 eq, 6.54 mmol), followed by 2-bromopropane (1 ml, 10.3 mmol). The reaction mixture was stirred at room temperature for 24 h, when DCM:ether:MeOH (55:40:5), indicated that the reaction had gone to completion. The solvent was evaporated in vacuo and the residue partitioned between EtOAc (100 ml) and water (100 ml). The aqueous phase was extracted with more EtOAc (2×50 ml) and the combined organic phase washed with brine (50 ml), dried (MgSO$_4$) and evaporated in vacuo. The residue was purified by silica gel flash column chromatography, eluted with CHCl$_3$:MeOH (98:2) to afford the title compound as a colorless film (350 mg, 77%). $\delta_H$ (CDCl$_3$, 500 MHz) 1.5 (6 H, d, J 7.5, CH[CH$_3$]$_2$), 4.7-4.6 (3 H, m, NHCH$_2$ and CHMe$_2$), 7.16 (1 H, d, J 2.5, ArH), 7.25 (1 H, s, br, NH), 7.66 (2 H, s, br, ArH), 8.67 (1 H, s, br, ArH); $\delta_C$ (CDCl$_3$, 500 MHz) 158.8 (C), 156.72 (C), 156.3 (C), 147.42 (CH), 137.92 (CH), 138.08

(CH), 131.73 (C), 123.31 (CH), 119.25 (C), 48.38 (CH), 44.1 (CH$_2$), 22.72 (2×CH$_3$); m/z 355.1 (M+H)

2R,3S-3-(9-Isopropyl-6-((6-(trifluoromethyl)pyridine-3-yl)methylamino)-9H-purin-2-ylamino)pentan-2-ol [11]

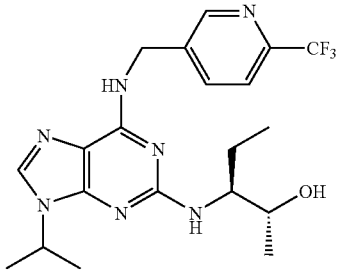 [SMILES: CC[C@H](Nc1nc(NCc2ccc(C(F)(F)F)nc2)c2ncn(C(C)C)c2n1)[C@@H](C)O]

To a stirred solution of 2-fluoro-9-isopropyl-N-(6-(trifluoromethylpyridin-3-ylmethyl)-9-H-purin-6-amine (200 mg, 0.56 mmol) in n-BuOH/DMSO (5 ml, 4:1) at room temperature under an argon atmosphere was added DIEA (1.4 ml, 10 eq, 8 mmol) followed by (2R,3S)-3-amino-pentan-2-ol (0.25 g, 2.4 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a colorless oil (30 mg, 12%). δ$_H$ (CDCl$_3$, 500 MHz) 0.85 (3 H, t, J 7.5, CHCH$_2$CH$_3$), 1.12 (3 H, d, J 5, CHCH$_3$OH), 1.52 (6 H, d, J 7.5, CH[CH$_3$]$_2$), 1.61-1.41 (2 H, m, CHCH$_2$CH$_3$), 3.82 (1 H, m, CHMe$_2$), 4.75-4.57 (1 H, m, CHCH$_3$OH), 4.82-4.64 (2 H, m, NHCH$_2$Ar), 5.8 (1H, s, br, NH), 6.85 (1 H, s, br, NH), 7 (1 H, d, J 10, ArH), 7.31-7.23 (2 H, m, ArH), 8.45 (1 H, s, br, ArH); δ$_C$ (CDCl$_3$, 250 MHz) 158.61 (C), 157.35 (C), 156.97 (C), 147.62 (CH), 137.43 (CH), 129.22 (C), 128.72 (C), 128.92 (CH), 1231.14 (CH), 118.32 (C), 69.64 (CH), 60.91 (CH$_2$), 57.68 (CH), 23.55 (CH$_2$), 22.53 (2×CH$_3$), 12.12 (CH$_3$); m/z 438.3 (M+H)

Example 12

2-Fluoro-N-((6-methylpyridin-2-yl)methyl)-9H-purin-6-amine

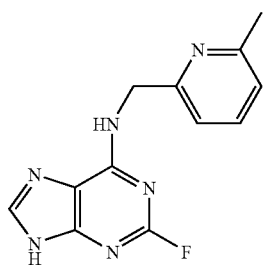 [SMILES: Cc1cccc(CNc2nc(F)nc3[nH]cnc23)n1]

To a stirred solution of 6-chloro-2-fluoropurine (0.4 g, 2.3 mmol) in n-BuOH (50 ml) under an argon atmosphere at 0° C., was added DIEA (2.5 ml, 14.7 mmol) followed by (6-methylpyridin-2-yl)methanamine (0.36 g, 2.95 mmol). The reaction mixture was stirred at this temperature for 1 h and then allowed to return to room temperature and stirred for 4 h, it was still seen incomplete, hence heated the reaction to 100° C. and left at that temperature for 8 h. The solvent was evaporated in vacuo and the residue was purified by gradient flash column chromatography on silica gel, eluted with CHCl$_3$:MeOH (100:0→90:10), to afford the product as a white solid; Yield: 0.35 g (60%). δ$_H$ (CDCl$_3$, 500 MHz) 2.44 (3 H, s, CH$_3$), 4.83-4.54 (3 H, m, NH and NHCH$_2$), 7.1-7.05 (2 H, m, ArH), 7.61-7.55 (1 H, m, ArH), 8.13-8.09 (1 H, m, ArH), 8.61 (1 H, s, br, NH); δ$_C$ (CDCl$_3$, 500 MHz) 159.41 (C), 158.78 (C), 158.53 (C), 157.19 (C), 155.38 (C), 147.69 (CH), 137.03 (C), 136.93 (CH), 121.34 (CH), 117.76 (CH), 117.31 (C), 46.47 (CH$_2$), 23.9 (CH$_3$); m/z 259.2 (M+H)

2-Fluoro-9-isopropyl-N-((6-methylpyridin-2-yl)methyl)-9H-purin-6-amine

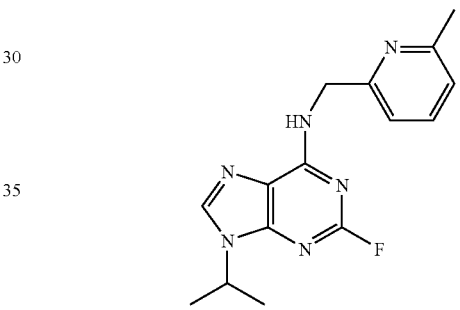

To a stirred solution of 2-fluoro-N-(6-methylpyridin-2-yl)methyl-9H-purin-6-amine (0.3 g, 1.17 mmol) in dimethylformamide (10 ml) at room temperature under an argon atmosphere, was added powdered, anhydrous K$_2$CO$_3$ (0.8 g, 5 eq, 5.85 mmol), followed by 2-bromopropane (1.15 ml, 11.7 mmol). The reaction mixture was stirred at room temperature for 24 h, when DCM:ether:MeOH (55:40:5), indicated that the reaction had gone to completion. The solvent was evaporated in vacuo and the residue partitioned between EtOAc (100 ml) and water (100 ml). The aqueous phase was extracted with more EtOAc (2×50 ml) and the combined organic phase washed with brine (50 ml), dried (MgSO$_4$) and evaporated in vacuo. The residue was purified by silica gel column chromatography, eluted with CHCl$_3$:MeOH (98:2) to afford the title compound as a slightly yellow film (180 mg, 51%). δ$_H$ (CDCl$_3$, 500 MHz) 1.6 (6 H, d, J 7.5, CH[CH$_3$]$_2$), 2.54 (3 H, s, CH$_3$), 4.86-4.73 (3 H, m, NHCH$_2$ and CHMe$_2$), 7.06 (1 H, d, J 10, ArH), 7.14 (1H, d, J 10, ArH), 7.53 (1 H, t, J 10, ArH), 7.8 (1 H, s, ArH); δ$_C$ (CDCl$_3$, 500 MHz) 158.42 (C), 158.04 (C), 156.16 (C), 156 (C), 155.49 (C), 150.12 (C), 137.67 (CH), 136.93 (CH), 121.89 (CH), 118.1 (C), 118.53 (CH), 47.15 (CH), 45.52 (CH$_2$), 24.38 (CH$_3$), 22.58 (2×CH$_3$); m/z 301.2 (M+H); $^{19}$F NMR δ −50.22

2R,3S-3-(9-Isopropyl-6-((6-methylpyridin-2-yl)methylamino)-9H-purin-2-ylamino)pentan-2-ol [12]

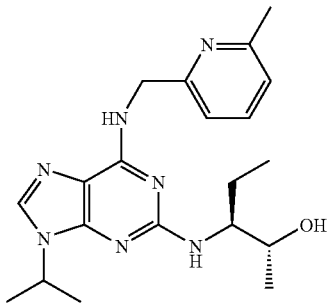 [SMILES: CC[C@H](Nc1nc(NCc2cccc(C)n2)c2ncn(C(C)C)c2n1)[C@@H](C)O]

To a stirred solution of 2-fluoro-9-isopropyl-N-(6-methylpyridin-2-ylmethyl)-9-H-purin-6-amine (180 mg, 0.59 mmol) in n-BuOH/DMSO (5 mL, 4:1) at room temperature under an argon atmosphere was added DIEA (1 ml, 10 eq, 5.6 mmol) followed by (2R,3S)-3-amino-pentan-2-ol (0.34 g, 6 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a slight yellow oil (28 mg, 13%) $\delta_H$ (CDCl$_3$, 500 MHz) 1.05 (3 H, t, J 7.5, CHCH$_2$CH$_3$), 1.13 (3 H, d, J 5, CHCH$_3$OH), 1.43 (6 H, d, J 7.5, CH[CH$_3$]$_2$), 1.6-1.4 (2 H, m, CHCH2CH3), 1.75 (1 H, s, br, NH), 2.32 (3 H, s, ArCH$_3$), 3.95 (1 H, s, br, CHMe$_2$), 4.57-4.53 (1 H, m, CHCH3OH), 4.8-4.6 (2 H, m, NHCH$_2$Ar), 5.8 (1 H, s, br, NH), 6.82 (1 H, s, br, NH), 6.95 (1 H, d, J 5, ArH), 7.05 (1 H, d, J 5, ArH), 7.45-7.4 (2 H, m, ArH); $\delta_C$(CDCl$_3$, 500 MHz) 160.17 (C), 157.9 (C), 156.72 (C), 154.8 (C), 150.12 (C), 136.8 (CH), 134.55 (CH), 121.64 (CH), 118.58 (CH), 114.87 (C), 71.59 (CH), 59.66 (CH), 46.41 (CH), 44.79 (CH$_2$), 24.12 (CH$_2$), 23.41 (CH$_3$), 21.59 (CH$_3$), 16.18 (CH$_3$), 10.6 (CH$_3$); m/z 384.3 (M+H)

Example 13

2-Fluoro-N-((3-methylpyridin-2-yl)methyl)-9H-purin-6-amine

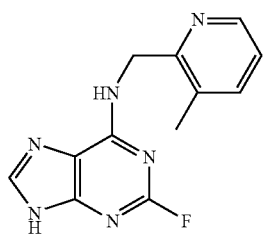 [SMILES: Cc1cccnc1CNc1nc(F)nc2[nH]cnc12]

To a stirred solution of 6-chloro-2-fluoropurine (0.4 g, 2.3 mmol) in n-BuOH (50 ml) under an argon atmosphere at 0° C., was added DIEA (2.5 ml, 14.7 mmol) followed by (3-methylpyridin-2-yl)methanamine (0.36 g, 2.95 mmol). The reaction mixture was stirred at this temperature for 1 h and then allowed to return to room temperature and stirred for 4 h, it was still seen incomplete, hence heated the reaction to 100° C. and left at that temperature for 8 h. The solvent was evaporated in vacuo and the residue was purified by gradient column chromatography on silica gel, eluted with CHCl$_3$:MeOH (100:0→90:10), to afford the product as a white solid; Yield: 0.3 g (51%). $\delta_H$(CDCl$_3$, 500 MHz) 2.35 (3 H, s, CH$_3$), 4.71 (3 H, m, NH and NHCH$_2$), 7.24 (1 H, s, br, ArH), 7.63 (1 H, s, br, ArH), 8.28 (1 H, s, br, ArH), 8.38 (1 H, s, br, ArH); $\delta_C$ (CDCl$_3$, 500 MHz) 161.03 (C), 158.49 (C), 154.77 (C), 152.16 (C), 144.86 (CH), 137.53 (CH), 137.14 (CH), 130.67 (C), 121.58 (CH), 118.73 (C), 42.87 (CH$_2$), 18.16 (CH$_3$); m/z 259.3 (M+H)

2-Fluoro-9-isopropyl-N-((3-methylpyridin-2-yl)methyl)-9H-purin-6-amine

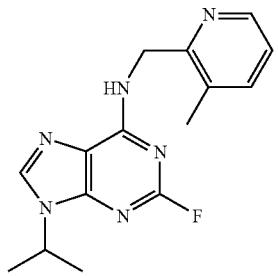 [SMILES: Cc1cccnc1CNc1nc(F)nc2c1ncn2C(C)C]

To a stirred solution of 2-fluoro-N-(3-methylpyridin-2-yl)methyl-9H-purin-6-amine (0.3 g, 1.17 mmol) in dimethylformamide (10 ml) at room temperature under an argon atmosphere, was added powdered, anhydrous K$_2$CO$_3$ (0.8 g, 5 eq, 5.85 mmol), followed by 2-bromopropane (1.15 ml, 11.7 mmol). The reaction mixture was stirred at room temperature for 24 h, when DCM:ether:MeOH (55:40:5), indicated that the reaction had gone to completion. The solvent was evaporated in vacuo and the residue partitioned between EtOAc (50 ml) and water (50 ml). The aqueous phase was extracted with more EtOAc (2×50 ml) and the combined organic phase washed with brine (50 ml), dried (MgSO$_4$) and evaporated in vacuo. The residue was purified by silica gel column chromatography, eluted with CHCl$_3$:MeOH (98:2) to afford the title compound as a slightly yellow film (170 mg, 48%). $\delta_H$ (CDCl$_3$, 500 MHz) 1.51 (6 H, d, J 7.5, CH[CH$_3$]$_2$), 2.28 (3 H, s, CH$_3$), 4.68-4.65 (3H, m, NHCH$_2$ and CHMe$_2$), 7.08-7.05 (1 H, m, ArH), 7.4 (1 H, d, J 5, ArH), 7.72 (1 H, s, ArH), 7.93 (1H, s, br, NH), 8.34 (1 H, d, J 5, ArH); $\delta_C$ (CDCl$_3$, 500 MHz) 160.09 (C), 158.43 (C), 155.97 (C), 154.06 (C), 145.85 (CH), 137.73 (CH), 137.54 (CH), 130.67 (C), 122.28 (CH), 118.73 (C), 47.28 (CH), 42.87 (CH$_2$), 22.43 (2×CH$_3$), 17.66 (CH$_3$); $^{19}$F NMR $\delta$ −50.20; m/z 301.2 (M+H)

2R,3S-3-(9-Isopropyl-6-((3-methylpyridin-2-yl)methylamino)-9H-purin-2-ylamino)pentan-2-ol [13]

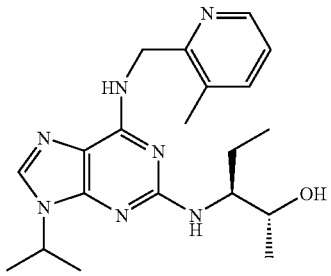 [SMILES: CC[C@H](Nc1nc(NCc2ncccc2C)c2ncn(C(C)C)c2n1)[C@@H](C)O]

To a stirred solution of 2-fluoro-9-isopropyl-N-(3-methylpyridin-2-ylmethyl)-9-H-purin-6-amine (170 mg, 0.56 mmol) in n-BuOH/DMSO (5 ml, 4:1) at room temperature under an argon atmosphere was added DIEA (1 ml, 10 eq, 5.6 mmol) followed by (2R,3S)-3-amino-pentan-2-ol (0.34 g, 6 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 mL), dried (MgSO$_4$) and evaporated in vacuo. The residue was purified by gradient flash column chromatography on silica gel eluted with CHCl$_3$:MeOH (100:0→95:5), to afford the title compound as a slight yellow oil (28 mg, 13%) δ$_H$ (CDCl$_3$, 500 MHz) 1 (3H, t, J 7.5, CHCH$_2$CH$_3$), 1.1 (3 H, d, J 5, CHCH$_3$OH), 1.44 (6 H, d, J 7.5, CH[CH$_3$]$_2$), 1.6-1.4 (2 H, m, CHCH$_2$CH$_3$), 1.75 (1 H, s, br, NH), 2.3 (3 H, s, ArCH$_3$), 3.92 (1 H, s, br, CHMe$_2$), 4.56-4.52 (1H, m, CHCH$_3$OH), 4.7 (2 H, s, br, NHCH$_2$Ar), 6.1 (1 H, s, br, NH), 7.06 (1H, dd, J 2.5, 5, ArH), 7.41 (1 H, dd, J 2.5, 5, ArH), 7.47 (1 H, s, ArH), 8.37 (1 H, d, J 5, ArH); δ$_C$ (CDCl$_3$, 500 MHz) 160.21 (C), 154.68 (C), 153.65 (C), 146.07 (CH), 137.53 (CH), 134.53 (CH), 130.59 (C), 122.31 (C), 122.13 (CH), 115.14 (C), 71.73 (CH), 59.93 (CH), 46.43 (CH), 43.11 (CH$_2$), 25.33 (CH$_2$), 22.63 (CH$_3$), 17.61 (CH$_3$), 17.25 (CH$_3$), 11.67 (CH$_3$); m/z 384.3 (M+H)

Example 14

(R)-1-(9-Isopropyl-6-(pyridin-3-ylmethylamino)-9H-purin-2-ylamino)propan-2-ol [14]

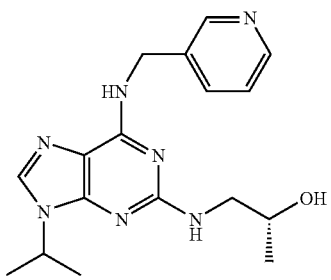 [SMILES: CC(C)n1cnc2c(NCc3cccnc3)nc(NC[C@@H](C)O)nc21]

To a stirred solution of 2-fluoro-9-isopropyl-6-[(pyridin-3-ylmethyl)-amino]purine (300 mg, 1.05 mmol) in n-BuOH/DMSO (5 ml, 4:1) at room temperature under an argon atmosphere was added DIEA (2 ml, 10 eq, 10.5 mmol) followed by (R)-1-aminopropan-2-ol (395 mg, 5.25 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between ethyl acetate (50 mL) and water (50 mL), the aqueous phase was extracted with more ethyl acetate (2×25 mL), and the combined organic phase was washed with brine (50 mL), dried (MgSO$_4$) and evaporated in vacuo. The residue was purified by gradient flash column chromatography on silica gel eluted with CHCl$_3$:MeOH (100:0→95:5), to afford the pure product as a colorless oil (38 mg, 10.6%). δ$_H$ (250 MHz, CDCl$_3$) 1.15 (3 H, d, J 7.5, CHCH$_3$OH), 1.45 (6 H, d, J 7.5, CH[CH$_3$]$_2$), 3.3-3.2 (1 H, m, NHCHHCHMeOH)), 3.45-3.36 (1 H, m, NHCHHCHMeOH), 3.96-3.9 (1 H, m, CHMe$_2$), 4.58-4.47 (1 H, m, CHMeOH), 4.69 (2 H, d, J 5, NHCH$_2$Ar), 5.23 (1 H, t, J 5, NHCH$_2$CHMeOH), 6.32 (1 H, s, br, NHCH$_2$Ar), 7.16-7.11 (1 H, m, ArH), 7.4 (1 H, s, ArH), 7.6 (1 H, d, J 7.5, ArH), 8.4 (1 H.d, J 2.5, ArH), 8.55 (1 H, s, ArH); δ$_C$ (250 MHz, CDCl$_3$) 160.07 (C), 154.95 (C), 154.7 (C), 151.1 (C), 149.27 (CH), 148.54 (CH), 135.3 (CH), 134.73 (CH), 123.39 (CH), 114.61 (C), 68.83 (CH), 50.09 (CH$_2$), 46.49 (CH), 41.95 (CH$_2$), 22.49 (2×CH$_3$), 20.85 (CH$_3$); m/z 342.2 (M+H)

Example 15

1,1,1-Trifluoro-3-(9-isopropyl-6-(pyridin-3-ylmethylamino)-9H-purin-2-ylamino)propan-2-ol [15]

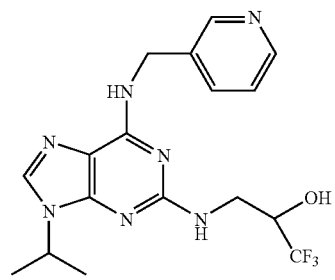 [SMILES: CC(C)n1cnc2c(NCc3cccnc3)nc(NCC(O)C(F)(F)F)nc21]

To a stirred solution of (2-fluoro-9-isopropyl-9H-purin-6-yl)-pyridin-3-ylmethyl-amine (300 mg, 1.05 mmol) in n-BuOH/DMSO (5 ml, 4:1) at room temperature under an argon atmosphere was added DIEA (1.4 ml, 10 eq, 8 mmol) followed by 3-amino-1,1,1-trifluoropropan-2-ol (1 g, 7.8 mmol) [prepared from the reaction of ammonia with 2-(trifluoromethyl)oxirane]. The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a colorless oil (62 mg, 15%). δ$_H$ (CDCl$_3$, 500 MHz) 1.53 (6 H, d, J 7.5, CH[CH$_3$]$_2$), 3.64-3.6 (1 H, m, NHCHHCOH[CF$_3$][CH$_3$]), 3.76-3.73 (1 H, m, NHCHHCOH[CF$_3$][CH$_3$]), 4.18-4.16 (1 H, m, CHMe$_2$), 4.62-4.56

(1 H, m, CHOHCF₃), 4.72 (3 H, s, br, NHCH₂Ar and N HCH₂Ar), 7.22-7.2 (1 H, m, ArH), 7.52 (1 H, s, ArH), 7.66 (1 H, d, J 10, ArH), 8.47 (1 H, d, J 5, ArH), 8.58 (1 H, s, ArH); δ_C (CDCl₃, 500 MHz) 159.77 (C), 154.68 (C), 149.04 (CH), 148.45 (CH), 135.44 (CH), 135.03 (CH), 134.44 (C), 125.91 (C), 123.49 (CH), 114.78 (C), 71.57 (CH), 46.76 (CH), 42.94 (CH₂), 32.2 (CH₂), 22.47 (2×CH₃) ¹⁹FNMR δ −78.48; m/z 396.2 (M+H)

Example 16

1,1,1-Trifluoro-3-nitropentan-2-ol

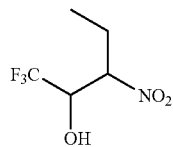

1-Nitropropane (3.25 g, 36.6 mmol), trifluoroacetaldehyde ethyl hemiacetal (5.85 g, 36.6 mmol, 90% purity) and powdered K₂CO₃ (0.34 g, 2.5 mmol) were mixed and stirred at 60° C. for 3 h and then at room temperature for 3 days. Brine (10 ml) and 1N aqueous HCl (10 ml) were added and the lower organic layer separated. The aqueous layer was extracted with ether (2×30 ml) and the combined organic layers were washed with brine, dried over Na₂SO₄, filtered and concentrated under vacuum. The residue was purified by flash chromatography on silica gel with a gradient elution of CH₂Cl₂:hexane (50:50), CH₂Cl₂:hexane (75:25), CH₂Cl₂ (100%) and MeOH:CH₂Cl₂ (5:95) to give the product as a waxy white solid (4.4 g, 64%). δ_H (CDCl₃, 500 MHz) 1.04-1.00 (3 H, m, CHCH₂CH₃), 2.16-1.99 (2 H, m, CHCH₂CH₃), 4.37 (1 H, s, b, OH), 4.71-4.59 (2 H, m, 2×CH); δ_C (CDCl₃, 500 MHz) dq (126.79, 126.70; 124.55, 124.46; 122.30, 122.21; 120.06, 119.96, CF₃), two peaks (88.34, 87.60 CH NO₂), eight peaks (71.13, 70.87, 70.81, 70.62, 70.56, 70.36, 70.30, 70.05 CHOH), two peaks (23.57 and 21.98 CH₂), two peaks (9.77 and 9.66 CH₃); 71.5 (CH), 54.03 (CH), 25.5 (CH₂), 11.05 (CH₃). ¹⁹F NMR δ −76.2 and −77.5

3-Amino-1,1,1-trifluoropentan-2-ol

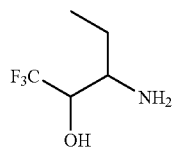

1,1,1-trifluoro-3-nitropentan-2-ol (3 g, 16 mmol) was dissolved in methanol (40 ml). Raney Nickel catalyst was added and the reaction vigorously stirred under an atmosphere of hydrogen for 24 h. The catalyst was filtered and the filtrate was concentrated in vacuo to give the amine relatively pure (2.35 g, 94%). δ_H (CDCl₃, 500 MHz) 1.05 (3 H, t, J 5, CHCH₂CH₃), 1.55-1.45 (1 H, m, CHCHHCH₃), 1.8-1.7 (1 H, m, CHCHHCH₃), 2.95-2.9 (1 H, m, CHEt), 3.95-3.85 (1 H, m, CHOHCF₃); δ_C (CDCl₃, 500 MHz) 124.5 (C), 71.5 (CH), 54.03 (CH), 25.5 (CH₂), 11.05 (CH₃)

1,1,1-Trifluoro-3-(9-isopropyl-6-(pyridin-3-ylmethylamino)-9H-purin-2-ylamino)pentan-2-ol [16]

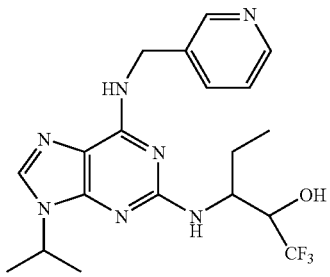 [SMILES: CCC(Nc1nc(NCc2cccnc2)c2ncn(C(C)C)c2n1)C(O)C(F)(F)F]

To a stirred solution of (2-fluoro-9-isopropyl-9H-purin-6-yl)-pyridin-3-ylmethyl-amine (300 mg, 1.05 mmol) in n-BuOH/DMSO (5 mL, 4:1) at room temperature under an argon atmosphere was added DIEA (1.4 ml, 10 eq, 8 mmol) followed by 3-amino-1,1,1-trifluoropentan-2-ol (1 g, 6.4 mmol). The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO₄) and evaporated in vacuo. The residue was purified by gradient flash column chromatography on silica gel eluted with CHCl₃:MeOH (100:0→95:5), to afford the title compound as a colorless film (42 mg, 9.4%). δ_H (CDCl₃, 500 MHz) 1.04 (3 H, t, J 7.5, CHCH₂CH₃) 1.56 (6 H, d, J 7.5, CH[CH₃]₂), 1.8-1.73 (2 H, m, CHCH₂CH₃), 4.13-4.07 (1 H, m, CHMe₂), 4.22-4.2 (1 H, m, CHEt) 4.57-4.55 (1 H, m, CHOHCF₃), 4.71 (2 H, s, b, NHCH₂Ar), 5.08 (1 H, s, b, NH), 7.2 (1 H, dd, J 5, 10 ArH), 7.51 (1H, s, ArH), 7.64 (1 H, d, J 10, ArH), 8.46 (1 H, d, J 5, ArH), 8.55 (1 H, s, ArH); δ_C (CDCl₃, 500 MHz) 159.28 (C), 154.72 (C), 149.07 (CH), 148.47 (CH), 135.44 (CH), 134.83 (C), 134.48 (CH), 124.12 (C), 123.44 (CH), 114.62 (C), 73.1 (CH), 55.88 (CH), 46.70 (CH), 41.78 (CH₂), 23.68 (CH₂) 22.36 (2×CH₃), 11.55 (CH₃); ¹⁹FNMR δ −74.83; m/z 424.2 (M+H)

Example 17

1,1,1-Trifluoro-3-(9-isopropyl-6-((6-(trifluoromethyl)pyridin-3-yl)methylamino)-9H-2-ylamino)pentan-2-ol [17]

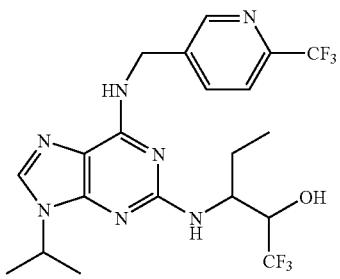 [SMILES: CCC(Nc1nc(NCc2ccc(C(F)(F)F)nc2)c2ncn(C(C)C)c2n1)C(O)C(F)(F)F]

To a stirred solution of 2-fluoro-9-isopropyl-N-(6-(trifluoromethylpyridin-3-ylmethyl)-9-H-purin-6-amine (200 mg, 0.56 mmol) in n-BuOH/DMSO (5 ml, 4:1) at room temperature under an argon atmosphere was added DIEA (1.4 ml, 10 eq, 8 mmol) followed by 3-amino-1,1,1-trifluoropentan-2-ol (0.377 g, 2.4 mmol). The flask was fitted with a condenser and the reaction mixture was placed in a preheated oil bath at 140° C. and stirred at this temperature for 72 h. After that time, the reaction has only gone by 30%. Addition of more aminoalcohol was done over four more days to get complete conversion. The reaction mixture was allowed to cool to room temperature and the solvent was evaporated in vacuo. The residue was partitioned between EtOAc (50 ml) and water (50 ml), the aqueous phase was extracted with more EtOAc (2×25 ml), and the combined organic phase was washed with brine (50 ml), dried (MgSO$_4$) and evaporated in vacuo. The residue was purified by gradient flash column chromatography on silica gel eluted with CHCl$_3$:MeOH (100:0→95:5), to afford the title compound as a brown powder (30 mg, 11%). $\delta_H$ (CDCl$_3$, 500 MHz) 0.95 (3H, t, J 7.5, CHCH$_2$CH$_3$), 1.56 (6 H, d, J 7.5, CH[CH$_3$]$_2$), 1.721-1.61 (2H, m, CHCH$_2$CH$_3$), 3.22-3.05 (1 H, m, CHEt), 3.88 (1 H, m, CHMe$_2$), 4.75-4.57 (1 H, m, CHCF$_3$OH), 4.92-4.76 (2 H, m, NHCH$_2$Ar), 5.3 (1 H, s, br, NH), 6.83 (1 H, s, br, NH), 7.55 (1 H, d, J 10, ArH), 7.61-7.53 (2H, m, ArH), 8.85 (1H, s, ArH); $\delta_C$ (CDCl$_3$, 250 MHz) 157.67 (C), 156.65 (C), 156.9 (C), 146.62 (CH), 139.55 (CH), 128.22 (C), 126.84 (C), 125.97 (CH), 123.14 (CH), 120.32 (C), 71.12 (CH), 61.56 (CH$_2$), 56.43 (CH), 25.74 (CH$_2$), 22.42 (2×CH$_3$), 11.56 (CH$_3$); $^{19}$F NMR $\delta$ −67.87, −74.30 ESMS 492 (M+1)

Example 18

1,1,1,3,3,3-Hexafluoro-2-((9-isopropyl-6-(pyridine-3-ylmethylamino)-9H-purin-2-ylamino)methyl)propan-2-ol [18]

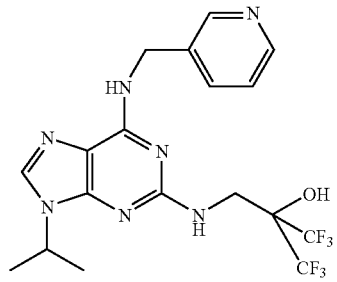 [SMILES: CC(C)n1cnc2c(NCc3cccnc3)nc(NCC(O)(C(F)(F)F)C(F)(F)F)nc21]

To a stirred solution of 2-fluoro-9-isopropyl-6-[(pyridine-3-ylmethyl)-amino]purine (50 mg, 0,175 mmol) in n-BuOH/DMSO (2.5 ml, 4:1) at room temperature and under an argon atmosphere was added diisopropylethylamine (135 mg, 1.05 mmol) followed by 2-(aminomethyl)-1,1,1,3,3,3-hexafluoropropane-2-ol (prepared from the reaction of 30% ammonium hydroxide with 2,2-bis[trifluoromethyl]oxirane). The reaction mixture was placed in a preheated oil bath at 140° C. and stirred at this temperature for 3 days. The reaction was followed by LCMS and was gone by only 30%. Additional newly prepared 2-(aminomethyl)-1,1,1,3,3,3-hexafluoropropane-2-ol was added and the reaction continued. This addition was done on three more consecutive days to achieve complete conversion. After removal of solvent, the residue was purified by silica gel flash column chromatography to give the title compound as a pale brown powder (19 mg, 23%); $\delta_H$ (CDCl$_3$, 500 MHz) 1.57 (6 H, d, J 7.5, CH[CH$_3$]$_2$), 3.48-3.44 (1 H, m, NHCHHCOH[CF$_3$]$_2$, 3.86-3.81 (1 H, m, NHCHHCOH[CF$_3$]$_2$), 4.62-4.555 (1 H, m, CHMe$_2$), 4.78-4.74 (2 H, m, NHCH$_2$ArH), 5.35 (1H, s, br, OH), 6.36 (1 H, s, br, NH), 7.27-7.22 (2 H, m, ArH), 7.7-7.67 (1 H, m, ArH), 8.5 (1 H, d, J 5, ArH), 8.66 (1 H, s, ArH); $\delta_C$ (CDCl$_3$, 500 MHz) 159.99 (C), 154.63 (C), 149.53 (C), 149.05 (C), 148.6 (CH), 137.79 (C), 135.41 (C), 135.38 (CH), 135 (CH), 123.44 (CH), 75.03 (C), 47.62 (CH$_2$), 46.84 (CH), 42.05 (CH$_2$), 22.1 (2×CH$_3$); m/z 464.2 (M+H)

Kinase Assays

A total of 21 compounds were evaluated in in vitro recombinant kinase assays and on tumour cells and compared with seliciclib. The majority of these cdk inhibitors were found to be more potent than seliciclib.

To evaluate the in-vitro kinase potency of the compounds, they were screened against CDK 2 and CDK9. Kinase assays were performed in 96-well plates using recombinant CDK/cyclins generated at Cyclacel. Ltd Dundee, UK. CDK2 and CDK9 assays were performed in a total volume of 25 µl in assay buffer (25 mM b-glycerophosphate, 20 mM MOPS, 5 mM EGTA, 1 mM DTT and 1 mM NaVO$_3$, pH 7.4), into which were added 2-4 µg of active enzyme with appropriate substrates (purified histone H1 for CDK2/cyclin E, and CDK2/cyclin A, biotinyl-Ahx-(YSPTSPS)$_4$ for CDK9/cyclin T1). The reaction was initiated by addition of Mg/ATP mix (15 mM MgCl$_2$+100 µM ATP with 30-50 kBq per well of [—$^{32}$P]-ATP) and mixtures incubated for 15 min (CDK2/cyclin E), 30 min (CDK2/cyclin A) or 45 min (CDK9/cyclin T1) as required, at 30° C. CDK2 reactions were stopped by addition of 25 µl of 75 mM phosphoric acid, followed by filtration through P81 filterplates (Whatman Polyfiltronics, Kent, UK). For CDK9, the reaction was stopped by addition of 25 µl of 75 mM phosphoric acid, then 5 µl of 10 mg/ml avidin was added to each well and further incubated for 2 min followed by filtration as per CDK2 assay. After washing 3 times with 75 mM orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 4.00, ID Business Solutions Ltd, Guildford, Surrey, UK) to determine IC$_{50}$ (concentration of compound which inhibits kinase activity by 50%). The average of duplicate points can be seen in Tables 2 and 4. The results show that many of the compounds are more potent inhibitors of CDK2 and CDK9 than the parent compound seliciclib.

Determination of IC$_{50}$ in H460 NSCLC Tumour Cell Line Using Alamar Blue Cytotoxicity Assay In order to determine the cellular potency of the compounds, the cytotoxicity of each compound was determined against the H460 non-small cell lung cancer (NSCLC) cell line. Standard cytotoxicity methods were performed as follows: H460 cells were seeded in 96-well plates appropriately for their doubling time (3000 cells per well) in RPMI media containing 10% FCS and incubated overnight at 37° C., 5% CO$_2$. The media was removed and 100 µl fresh media containing increasing concentrations of appropriate compound was added and the cells incubated for 72 hours at 37° C., 5% CO$_2$. A 10% stock of alamar blue (Roche, Lewes, United Kingdom) was prepared in medium and 100 µl added to the cells which were incubated for 2 hours. Absorbance was measured on the Wallac Victor 2 1420 multi-label counter at 544-595 nm. The average of three independent experiments is shown in Table 3.

Two compounds have IC$_{50}$ values less than 1 μM (compound [1] and compound [11]).

Comparison of the Mode of Action of Compounds of the Invention and Seliciclib

It has previously been shown that seliciclib induces apoptosis via its effects on transcription. Thus, seliciclib inhibits CDK7 and CDK9 which are responsible for the phosphorylation of RNA polymerase II, which is required for the initiation and elongation of transcription. As a result of the inhibition of transcription, the levels of a number of proteins with short half-lives decrease, such as Mcl-1, thereby triggering apoptosis.

To confirm that these compounds also caused Mcl-1 downregulation like seliciclib, H460 cells were seeded at 5×10$^5$ cells in 10 cm$^2$ plates in 10 ml RPMI media containing 10% FCS and incubated overnight at 37° C., 5% CO$_2$. 1 ml of 11× concentrated compound was then added to the cells which were incubated for 5 or 24 hours. The media was removed and the adherent cells washed with 5 ml PBS. Cells were lysed on the plates by addition of 100 μl lysis buffer (50 mM HEPES pH 7, 20 mM NaCl, 1 mM DTT, protease inhibitor cocktail (1:1000), and phosphatase inhibitors (10 mM sodium pyrophosphate, 10 mM sodium fluoride and 1 mM sodium orthovanadate). Lysates were snap-frozen in liquid nitrogen and stored at −70° C. Frozen lysates were thawed and sonicated 2×10 second bursts on ice. The protein concentration of each lysate was determined using the BCA protein determination kit (Pierce) as per the manufacturer's instructions. Lysate (30 μg) was mixed with 1× gel loading buffer containing 10% β-mercaptoethanol and separated in 4-12% Bis-Tris polyacrylamide gels using denaturing electrophoretic conditions (Invitrogen, Glasgow, United Kingdom). Proteins were transferred to nitrocellulose membranes (Schleicher & Schuell, Dassel, Germany) using wet electrophoretic transfer. Membranes were stained with Ponceau S to confirm equal loading before blocking in 5% nonfat milk in PBS with 0.05% Tween 20 (PBSTM) for 2 hours. Membranes were incubated overnight at 4° C. with primary antibody (rabbit polyclonal antibody to Mcl-1, Santa Cruz), diluted 1:1000 in PBSTM. Membranes were washed 2×5 minute followed by 2×10 minute in PBS and 0.05% Tween 20 (PBST) and incubated for 1 hour in PBSTM containing horseradish peroxidase-conjugated secondary antibody. Membranes were washed as before and incubated with enhanced chemiluminescence solution (Amersham) and exposed to X-ray film (Amersham).

As expected, seliciclib only shows very modest changes since the top concentration used in this experiment is close to the IC$_{50}$ value for this compound. Compound [1] appears superior to seliciclib in its ability to decrease Mcl-1 levels with significant effects observed at 1.5 μM at 24 hr. This is in agreement with its increased potency.

Figure 2:
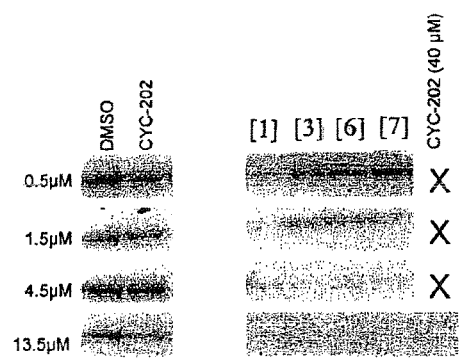
FIG. 2 shows the effect of the some of the follow-on compounds on Mcl-1 levels in H460 cells. Cells were treated with a range of concentrations of each drug and analysed after 5 hours.

In a second experiment the effect of additional compounds on Mcl-1 levels was investigated. In this case, H460 cells were treated with 0.5, 1.5, 4.5 and 13.5 μM for 5 hrs at which point the cells were harvested for western blotting analysis. The results are shown in FIG. 2.

The results show that compound [1] appears to be the most effective compound from this group in downregulating the levels of Mcl-1 and has superior potency to seliciclib. However, it is clear that all of these compounds cause a decrease in Mcl-1 at concentrations equivalent to approximately 2-3 times their IC$_{50}$ value.

Cytochrome P450s Inhibition (5 Isoform IC$_{50}$ Determination)

Objective

To identify whether compound [1] inhibits the activity of five CYP isoforms by the analysis of the metabolism of CYP specific substrates. Comparative studies were carried out using prior art compounds [A1], [A2] and [A3] shown below:

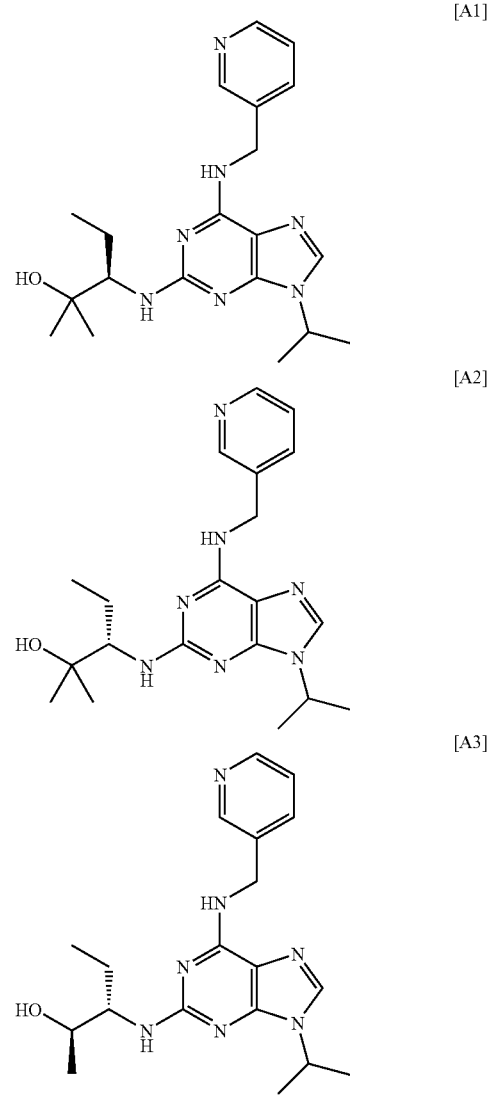

Experimental Procedure

Compound [A1], [A2] and [A3] were synthesised in accordance with the methods set forth in WO 2004/016612 (Cyclacel Limited).

CYP1A Inhibition

Six test compound concentrations (0.05, 0.25, 0.5, 2.5, 5, 25 μM in DMSO; final DMSO concentration=0.35%) were incubated with human liver microsomes (0.25 mg/mL) and NADPH (1 mM) in the presence of the probe substrate ethoxyresorufin (0.5 μM) for 5 min at 37° C. The selective CYP1A inhibitor, alpha-naphthoflavone, was screened alongside the test compounds as a positive control.

CYP2C9 Inhibition

Six test compound concentrations (0.05, 0.25, 0.5, 2.5, 5, 25 μM in DMSO; final DMSO concentration=0.25%) were incubated with human liver microsomes (1 mg/mL) and NADPH (1 mM) in the presence of the probe substrate tolbutamide (120 μM) for 60 min at 37° C. The selective CYP2C9 inhibitor, sulphaphenazole, was screened alongside the test compounds as a positive control.

CYP2C19 Inhibition

Six test compound concentrations (0.05, 0.25, 0.5, 2.5, 5, 25 μM in DMSO; final DMSO concentration=0.25%) were incubated with human liver microsomes (0.5 mg/mL) and NADPH (1 mM) in the presence of the probe substrate mephenyloin (25 μM) for 60 min at 37° C. The selective CYP2C19 inhibitor, tranylcypromine, was screened alongside the test compounds as a positive control.

CYP2D6 Inhibition

Six test compound concentrations (0.05, 0.25, 0.5, 2.5, 5, 25 μM in DMSO; final DMSO concentration=0.25%) were incubated with human liver microsomes (0.5 mg/mL) and NADPH (1 mM) in the presence of the probe substrate dextromethorphan (5 μM) for 30 min at 37° C. The selective CYP2D6 inhibitor, quinidine, was screened alongside the test compounds as a positive control.

CYP3A4 Inhibition

Six test compound concentrations (0.05, 0.25, 0.5, 2.5, 5, 25 μM in DMSO; final DMSO concentration 0.26%) were incubated with human liver microsomes (0.25 mg/mL) and NADPH (1 mM) in the presence of the probe substrate midazolam (2.5 μM) for 5 min at 37° C. The selective CYP3A4 inhibitor, ketoconazole, was screened alongside the test compounds as a positive control.

For the CYP1A incubations, the reactions were terminated by the addition of methanol, and the formation of the metabolite, resorufin, was monitored by fluorescence (excitation wavelength=535 nm, emission wavelength=595 nm). For the CYP2C9, CYP2C19, CYP2D6, and CYP3A4 incubations, the reactions were terminated by the addition of methanol containing internal standard. The samples were then centrifuged, and the supernatants were combined, for the simultaneous analysis of 4-hydroxytolbutamide, 4-hydroxymephenyloin, dextrorphan, and 1-hydroxymidazolam plus internal standard by LC-MS/MS using generic LC-MS/MS conditions. Formic acid in deionised water (final concentration=0.1%) was added to the final sample prior to analysis. A decrease in the formation of the metabolites compared to vehicle control was used to calculate an $IC_{50}$ value (test compound concentration which produces 50% inhibition).

Results

The $IC_{50}$ (μM), for each compound against the five CYP isoforms are shown in Table 5.

The data indicate that three compounds are significant inhibitors of CYP3A4 while compound [1] is not. Since the compound [1] $IC_{50}$ value is significantly above its cellular $IC_{50}$ (see Table 7) this indicates that at cytotoxic concentrations there should be no effect on CYP3A4 activity. This is important because CYP3A4 is involved in the metabolism of a large number of medications. If CYP3A4 is inhibited by one drug this can lead to unexpected toxicity due to reduced metabolism of CYP3A4 substrates, thereby resulting in apparent increased levels of these agents.

Cytochrome P450 Substrate Identification

Objective

To identify which of the major cytochrome P450 isoforms are involved in the metabolism of the four test compounds.

Experimental Procedure cDNA expressed human CYP450 enzyme preparations co-expressed with human NADPH cytochrome P450 reductase (Bactosomes™) were supplied by Cypex Ltd. Bactosomes™ (final P450 concentration CYP1A2 100 pmol/mL, CYP2C8 50 pmol/mL, CYP2C9 25 pmol/mL, CYP2C19 100 pmol/mL, CYP2D6 50 pmol/mL and CYP3A4 25 pmol/mL), 0.1M phosphate buffer pH7.4 and test compound (final substrate concentration=5 μM; final DMSO concentration=0.25%) were pre-incubated at 37° C. prior to the addition of NADPH (final concentration=1 mM) to initiate the reaction. Incubations were also performed using control bactosomes (no P450 enzymes present) to reveal any non-enzymatic degradation. The final incubation volume was 25 μL. Compounds known to be metabolised specifically by each CYP450 isoform were used as control compounds.

Each compound was incubated singly for 0, 5, 15, 30 and 45 min with each CYP isoform. The reactions were stopped by the addition of 50 μL methanol containing internal standard at the appropriate time points. The incubation plates were centrifuged at 2500 rpm for 20 min at 4° C. to precipitate the protein. Following protein precipitation, the sample supernatants were combined in cassettes of up to four compounds and analysed using generic LC-MS/MS conditions.

Data Analysis

The In peak area ratio (which has been corrected for any loss in the incubations with the control bactosomes) was plotted against time and the gradient of the line determined.

The elimination rate constant (k)=(−gradient)

$$\text{Half life } (t_{1/2}) \text{ (min)} = \frac{0.693}{k}$$

Results

The half life (mins) for each compound in the presence of each of six CYPs are shown in Table 6.

The data indicate that in this Bactosomes™ system, compound [1] is not a substrate for the six CYP isoforms tested. There is a major difference with the other three compounds because they are all substrates of CYP3A4 and two are also substrates of CYP1A2. This difference corresponds well with the difference in CYP inhibition discussed in Table 4. A common mechanism leading to CYP inhibition is if the compound is also a substrate for that CYP. As can be seen, compound [1] in neither a substrate of nor inhibitor of CYP3A4 whereas the other three compounds are.

Kinase Assays

To evaluate the in-vitro kinase potency of the compounds, they were screened against CDK 2 and CDK9. Kinase assays were performed in 96-well plates using recombinant CDK/cyclins generated at Cyclacel. Ltd Dundee, UK. CDK2 and CDK9 assays were performed in a total volume of 25 μl in assay buffer (25 mM b-glycerophosphate, 20 mM MOPS, 5 mM EGTA, 1 mM DTT and 1 mM $NaVO_3$, pH 7.4), into which were added 2-4 μg of active enzyme with appropriate substrates (purified histone H1 for CDK2/cyclin E, and CDK2/cyclinA, biotinyl-Ahx-$(YSPTSPS)_4$ for CDK9/cyclin T1). The reaction was initiated by addition of Mg/ATP mix (15 mM $MgCl_2$+100 μM ATP with 30-50 kBq per well of [−$^{32}$P]-ATP) and mixtures incubated for 15 min (CDK2/cyclin E), 30 min (CDK2/cyclin A) or 45 min (CDK9/cyclin T1) as required, at 30° C. CDK2 reactions were stopped by addition of 25 μl of 75 mM phosphoric acid, followed by filtration through P81 filterplates (Whatman Polyfiltronics, Kent, UK). For CDK9, the reaction was stopped by addition of 25 μl of 75 mM phosphoric acid, then 5 μl of 10 mg/ml avidin was added to each well and further incubated for 2 min followed by filtration as per CDK2 assay. After washing 3 times with 75 mM orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 4.00, ID Business Solutions Ltd, Guildford, Surrey, UK) to determine IC$_{50}$ (concentration of compound which inhibits kinase activity by 50%). The average of duplicate points can be seen in Tables 6 and 8.

Results

The results in Table 7 show prior art compound [A3] and compound [1] are the most potent kinase inhibitors.

Determination of IC$_{50}$ in Tumour Cell Lines Using Alamar Blue Cytotoxicity Assay In order to determine the cellular potency of the compounds, the cytotoxicity of each compound was determined against a range of cell lines. Standard cytotoxicity methods were performed as follows: cells were seeded in 96-well plates appropriately for their doubling time (2-5000 cells per well) in RPMI or DMEM media containing 10% FCS and incubated overnight at 37° C., 5% CO2. The media was removed and 100 µl fresh media containing increasing concentrations of appropriate compound was added and the cells incubated for 72 hours at 37° C., 5% $CO_2$. A 10% stock of alamar blue (Roche, Lewes, United Kingdom) was prepared in medium and 100 µl added to the cells which were incubated for 2 hours. Absorbance was measured on the Wallac Victor 2 1420 multi-label counter at 544-595 nm.

Results

The results for cellular cytotoxicity analysis against 21 cell lines are shown in Table 8. Compound [1] is significantly more potent than prior art compounds [A1], [A2] or [A3].

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1

| Compound | Structure | Name |
|---|---|---|
| [1] | 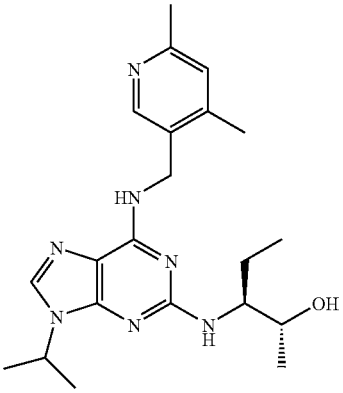 [SMILES: CC[C@H](Nc1nc(NCc2cnc(C)cc2C)c2ncn(C(C)C)c2n1)[C@@H](C)O] | (2R,3S-3-(6-((4,6-Dimethylpyridin-3-ylmethylamino)-9-isopropyl-9H-purin-2-ylamino)pentan-2-ol |
| [2] | 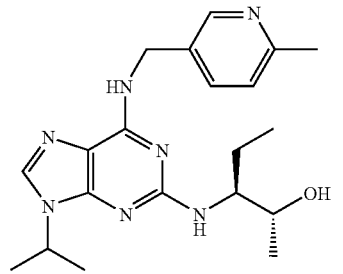 [SMILES: CC[C@H](Nc1nc(NCc2ccc(C)nc2)c2ncn(C(C)C)c2n1)[C@@H](C)O] | 2R,3S-3-(9-isopropyl-6-((6-methylpyridin-3-yl)methylamino)-9H-purin-2-ylamino)pentan-2-ol |
| [3] | 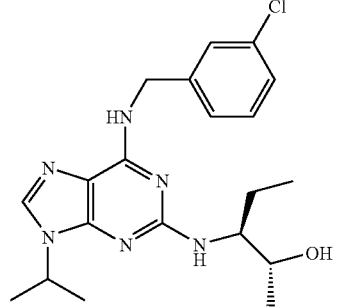 | 2R,3S-3-(6-(3-Chlorobenzylamino)-9-isopropyl-9H-purin-2-ylamino)pentan-2- |

TABLE 1-continued

Selected compounds of the invention

| Compound | Structure | Name |
| --- | --- | --- |
| [4] | 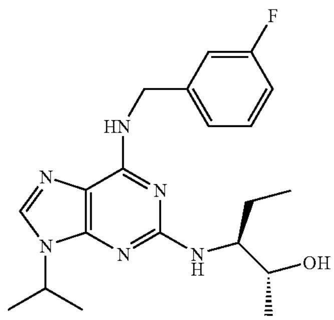 [SMILES: CC[C@H](Nc1nc(NCc2cccc(F)c2)c2ncn(C(C)C)c2n1)[C@@H](C)O] | 2R,3S-3-[6-(3-Fluorobenzylamino)-9-isopropyl-9H-purin-2-ylamino]-pentan-2-ol |
| [5] | 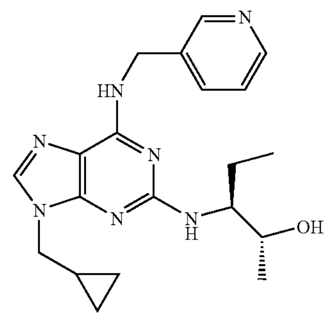 [SMILES: CC[C@H](Nc1nc(NCc2cccnc2)c2ncn(CC3CC3)c2n1)[C@@H](C)O] | 2R,3S-3-(9-(Cyclopropylmethyl)-6-(pyridin-3-ylmethylamino)-9H-purin-2-ylamino)pentan-2-ol |
| [6] | 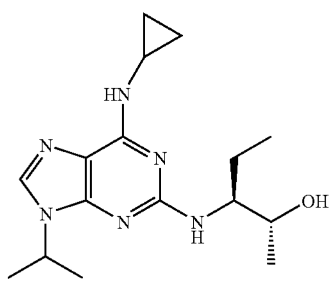 [SMILES: CC[C@H](Nc1nc(NC2CC2)c2ncn(C(C)C)c2n1)[C@@H](C)O] | 2R,3S-3-(6-Cyclopropylamino)-9-isopropyl-9H-purin-2-ylamino)pentan-2-ol |
| [7] | 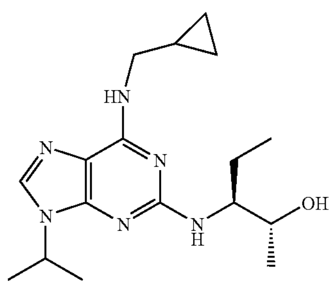 [SMILES: CC[C@H](Nc1nc(NCC2CC2)c2ncn(C(C)C)c2n1)[C@@H](C)O] | 2R,3S-3-(6-(Cyclopropylmethylamino)-9-isopropyl-9H-purine-2-ylamino)pentan-2-ol |
| [8] | 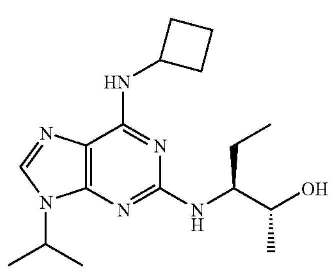 [SMILES: CC[C@H](Nc1nc(NC2CCC2)c2ncn(C(C)C)c2n1)[C@@H](C)O] | 2R,3S-3-(6-(Cyclobutylamino)-9-isopropyl-9H-purin-2-ylamino)pentan-2-ol |

TABLE 1-continued

Selected compounds of the invention

| Compound | Structure | Name |
|---|---|---|
| [9] | 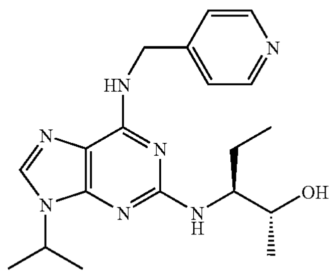 [SMILES: CC[C@H](Nc1nc(NCc2ccncc2)c2ncn(C(C)C)c2n1)[C@@H](C)O] | 2R,3S-3-(9-Isopropyl-6-(pyridine-4-ylmethylamino)-9H-purin-2-ylamino)pentan-2-ol |
| [10] | 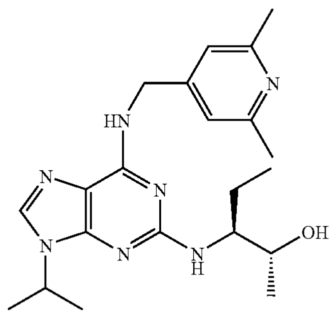 [SMILES: CC[C@H](Nc1nc(NCc2cc(C)nc(C)c2)c2ncn(C(C)C)c2n1)[C@@H](C)O] | 2R,3S-3-(9-Isopropyl-6-(2,6-dimethylpyridine-4-ylmethylamino)-9H-purin-2-ylamino)pentan-2-ol |
| [11] | 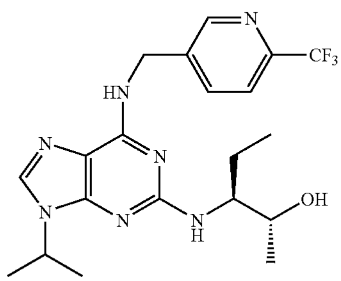 [SMILES: CC[C@H](Nc1nc(NCc2ccc(C(F)(F)F)nc2)c2ncn(C(C)C)c2n1)[C@@H](C)O] | 2R,3S-3-(9-Isopropyl-6-((6-(trifluoromethyl)pyridine-3-yl)methylamino)-9H-purin-2ylamino)pentan-2-ol |
| [12] | 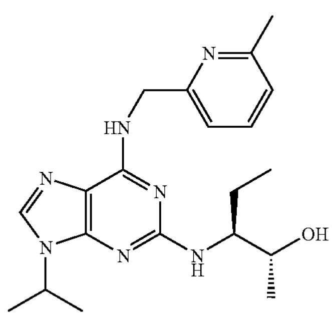 [SMILES: CC[C@H](Nc1nc(NCc2cccc(C)n2)c2ncn(C(C)C)c2n1)[C@@H](C)O] | 2R,3S-3-(9-Isopropyl-6-((6-methylpyridin-2-yl)methylamino)-9H-purin-2-ylamino)pentan-2-ol |
| [13] | 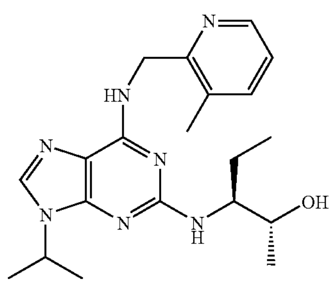 [SMILES: CC[C@H](Nc1nc(NCc2ncccc2C)c2ncn(C(C)C)c2n1)[C@@H](C)O] | 2R,3S-3-(9-Isopropyl-6-((3-methylpyridin-2-yl)methylamino)-9H-purin-2-ylamino)pentan-2-ol |

TABLE 1-continued

Selected compounds of the invention

| Compound | Structure | Name |
|---|---|---|
| [14] | 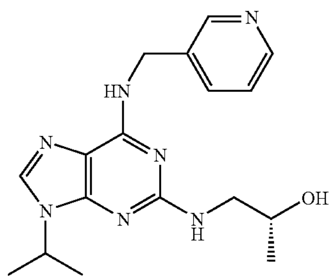 [SMILES: CC(C)n1cnc2c(NCc3cccnc3)nc(NC[C@@H](C)O)nc21] | (R)-1-(9-Isopropyl-6-(pyridin-3-ylmethylamino)-9H-purin-2-ylamino)propan-2-ol |
| [15] | 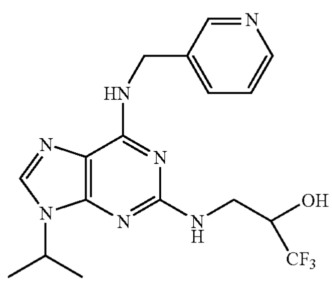 [SMILES: CC(C)n1cnc2c(NCc3cccnc3)nc(NCC(O)C(F)(F)F)nc21] | 1,1,1-Trifluoro-3-(9-isopropyl-6-(pyridin-3-ylmethylamino)-9H-purin-2-ylamino)propan-2-ol |
| [16] | 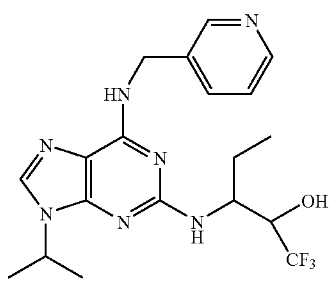 [SMILES: CCC(Nc1nc(NCc2cccnc2)c2ncn(C(C)C)c2n1)C(O)C(F)(F)F] | 1,1,1-Trifluoro-3-(9-isopropyl-6-(pyridin-3-ylmethylamino)-9H-purin-2-ylamino)pentan-2-ol |
| [17] | 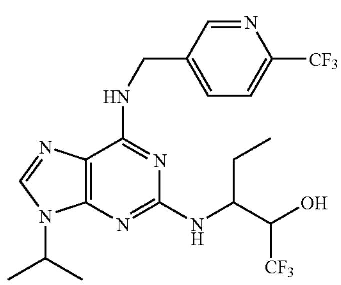 [SMILES: CCC(Nc1nc(NCc2ccc(C(F)(F)F)nc2)c2ncn(C(C)C)c2n1)C(O)C(F)(F)F] | 1,1,1-Trifluoro-3-(9-isopropyl-6-((6-(trifluoromethyl)pyridin-3-yl)methylamino)-9H-2-ylamino)pentan-2-ol |
| [18] | 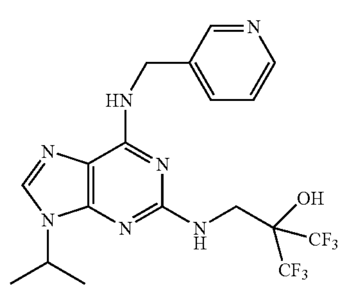 [SMILES: CC(C)n1cnc2c(NCc3cccnc3)nc(NCC(O)(C(F)(F)F)C(F)(F)F)nc21] | 1,1,1,3,3,3-Hexafluoro-2-((9-isopropyl-6-(pyridine-3-ylmethylamino)-9H-purin-2-ylamino)methyl)propan-2-ol |

TABLE 2

Summary of in-vitro kinase assay screen on second generation compounds and seliciclib.

| | CDK2/Cyclin E | | CDK2/Cyclin A | | CDK9/Cyclin T1 | |
|---|---|---|---|---|---|---|
| Compound | Average | SD | Average | SD | Average | SD |
| Seliciclib 1 | 0.42 | 0.08 | 1.50 | 0.11 | 2.03 | 0.35 |
| [1] | 0.02 | 0.001 | 0.09 | 0.00 | 0.10 | 0.02 |
| [2] | 0.52 | 0.15 | 3.25 | 1.03 | 3.63 | 0.76 |
| [3] | 0.01 | 0.004 | 0.10 | 0.004 | 0.06 | 0.00 |
| [4] | 0.02 | 0.01 | 0.12 | 0.01 | 0.08 | 0.02 |
| Seliciclib 2 | 0.28 | 0.03 | ND | ND | 2.35 | 0.61 |
| [5] | 0.83 | 0.22 | ND | ND | 7.89 | NA |
| [6] | 0.05 | 0.003 | ND | ND | 0.27 | 0.03 |
| [7] | 0.04 | 0.01 | ND | ND | 0.38 | 0.01 |
| [8] | 0.16 | 0.05 | ND | ND | 0.50 | 0.25 |
| [9] | 0.04 | 0.01 | ND | ND | 0.61 | 0.01 |
| [10] | 0.05 | 0.02 | ND | ND | 1.04 | 0.30 |
| [11] | 0.04 | 0.01 | ND | ND | 0.25 | 0.10 |
| [12] | 0.05 | 0.01 | ND | ND | 2.04 | 0.44 |
| [13] | 0.77 | 0.06 | ND | ND | 5.84 | 1.21 |
| [14] | 0.29 | 0.14 | ND | ND | 6.53 | 2.74 |
| [15] | 0.57 | 0.04 | ND | ND | 7.40 | 2.81 |
| [16] | 0.09 | 0.01 | ND | ND | 2.14 | 0.50 |

$IC_{50}$ values are expressed in μM. The compounds were analysed in 2 batches and in both cases seliciclib was run as a control in the assay, giving rise to seliciclib 1 and 2, which gave similar results.

TABLE 3

Summary table of cellular $IC_{50}$ values for the compounds as determined in H460 cells.

| Compound | Average IC50 (μM) | SD | Fold increase in potency |
|---|---|---|---|
| [1] | 0.5 | 0.0 | 24.0 |
| [2] | 35 | 5.5 | 0.3 |
| [3] | 1.5 | 0.1 | 8.0 |
| [4] | 1.5 | 0.1 | 8.0 |
| [5] | 34.4 | 3.2 | 0.3 |
| [6] | 1.7 | 0.2 | 7.1 |
| [7] | 2.4 | 0.7 | 5.0 |
| [8] | 2.9 | 0.6 | 4.1 |
| [9] | 2.3 | 0.3 | 5.2 |
| [10] | 2.4 | 0.1 | 5.0 |
| [11] | 0.9 | 0.2 | 13.3 |
| [12] | 7.2 | 0.1 | 1.7 |
| [13] | 19.4 | 5.3 | 0.6 |
| [14] | 16.7 | 2.3 | 0.7 |
| [15] | 20.3 | 5.2 | 0.6 |
| [16] | 4.1 | 0.6 | 2.9 |
| Seliciclib | 12.0 | 2.2 | NA |

The last column illustrates how much more potent many of these compounds are compared with seliciclib.

TABLE 4

Summary of in-vitro kinase assay screen on compounds [17] and [18] (μM)

| | CDK2E | | | | CDK2A | | | | CDK1B | | | |
|---|---|---|---|---|---|---|---|---|---|---|---|---|
| Cpd | Run 1 | Run 2 | Mean | SD | Run 1 | Run 2 | Mean | SD | Run 1 | Run 2 | Mean | SD |
| [17] | 0.318 | 0.307 | 0.313 | 0.008 | 0.305 | 0.431 | 0.368 | 0.089 | 6.121 | 11.235 | 8.678 | 3.616 |
| [018] | 0.336 | 0.279 | 0.308 | 0.040 | 0.704 | 1.194 | 0.942 | 0.347 | 5.882 | 6.725 | 6.303 | 0.596 |
| [017] | >10 | >10 | >10 | | 1.851 | 1.777 | 7.814 | 0.053 | 2.046 | 5.426 | 3.736 | 2.390 |
| [018] | >10 | >10 | >10 | | 5.045 | 6.009 | 5.527 | 0.682 | 3.954 | 3.210 | 3.582 | 0.526 |

TABLE 5

$IC_{50}$ (μM) for prior art compounds [A1], [A2] and [A3] and compound [1] of the invention against the five CYP isoforms

| | CYP1A | CYP2C19 | CYP2C9 | CYP2D6 | CYP3A4 |
|---|---|---|---|---|---|
| [A1] | >25 | 19.9 | >25 | >25 | 1.63 |
| [A2] | >25 | >25 | >25 | >25 | 0.48 |
| [A3] | >25 | >25 | >25 | >25 | 1.88 |
| [1] | >25 | >25 | 23.8 | >25 | 22.5 |

TABLE 6

The half life (mins) for prior art compounds [A1], [A2] and [A3] and compound [1] of the invention in the presence of each of six CYPs

| | CYP1A2 | CYP2C19 | CYP2C8 | CYP2C9 | CYP2D6 | CYP3A4 |
|---|---|---|---|---|---|---|
| [A1] | 29.2 | 58.3 | >45 | >45 | >45 | 28.3 |
| [A2] | 49.5 | >45 | >45 | >45 | >45 | 32.6 |
| [A3] | >45 | >45 | >45 | >45 | >45 | 18.0 |
| [1] | >45 | >45 | >45 | >45 | >45 | >45 |

TABLE 8

The results for cellular cytotoxicity analysis for prior art compounds [A1], [A2], [A3] and compound [1] of the invention against various cell lines

|  | [A1] | [A2] | [A3] | [1] |
|---|---|---|---|---|
| H1650 | 6.49 | 3.65 | 1.22 | 0.46 |
| B16 | 7.77 | 2.59 | 0.66 |  |
| HeLa | 6.64 | 3.30 |  |  |
| MDA-MB-436 | 6.6 | 3.38 | 0.97 | 0.44 |
| H2052 | 5.16 | 2.36 | 0.94 | 0.29 |
| LoVo | 4.50 | 2.20 | 0.82 | 0.70 |
| Saos-2 | 5.31 | 2.48 | 1.40 |  |
| CT26.WT | 6.69 | 4.88 | 1.63 |  |
| H292 | 6.56 | 2.34 | 0.91 | 0.37 |
| Colo205 | 4.48 | 2.31 | 0.82 | 0.31 |
| HT-29 | 4.15 | 1.70 | 1.17 |  |
| NCI-H460 | 2.80 | 2.21 | 0.70 | 0.50 |
| LP-1 |  | 1.64 | 0.47 |  |
| A549 | 2.95 | 1.60 | 0.47 | 0.16 |
| MESSA | 3.62 | 1.59 | 0.50 | 0.16 |
| MESSA-Dx5 | 14.69 | 8.52 | 3.87 | 1.21 |
| HCT 116 |  | 1.57 | 0.44 |  |
| MCF7 | 3.65 | 1.64 | 0.45 | 0.26 |
| NCI-H929 | 5.16 | 2.35 | 0.79 | 0.35 |
| A2780 | 2.60 | 1.10 | 0.38 | 0.41 |
| H358 | 2.69 | 0.84 | 0.33 | 0.18 |
| Ave | 4.88 | 2.29 | 0.79 | 0.35 |

The invention claimed is:

1. A compound of formula (I), or a pharmaceutically acceptable salt thereof,

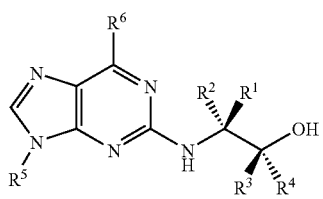

(I)

wherein:
$R^1$ and $R^2$ are each independently H, alkyl or haloalkyl;
$R^3$ and $R^4$ are each independently H, alkyl, haloalkyl or aryl;
$R^5$ is alkyl or cycloalkyl or cycloalkyl-alkyl, each of which may be optionally substituted with one or more OH groups;
$R^6$ is selected from cyclopropylamino, cyclopropylmethylamino, cyclobutylamino, cyclobutylmethylamino and

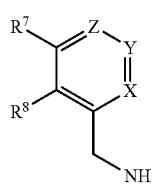

where one of X, Y and Z is N and the remainder are $CR^9$;
$R^7$, $R^8$ and each $R^9$ are independently H, alkyl or haloalkyl, wherein at least one of $R^7$, $R^8$ and each $R^9$ is other than H.

2. A compound according to claim 1 wherein one of $R^1$ and $R^2$ is H and the other is alkyl.

3. A compound according to claim 1 wherein one of $R^1$ and $R^2$ is H and the other is methyl, ethyl or isopropyl.

4. A compound according to claim 1 wherein $R^1$ is ethyl and $R^2$ is H.

5. A compound according to claim 1 wherein $R^3$ and $R^4$ are each independently H, alkyl, haloalkyl or aryl, and wherein at least one of $R^3$ and $R^4$ is other than H.

6. A compound according to claim 1 wherein one of $R^3$ and $R^4$ is H and the other is alkyl or haloalkyl.

7. A compound according to claim 1 wherein $R^3$ is H and $R^4$ is alkyl or haloalkyl.

8. A compound according to claim 1 wherein $R^3$ is H and $R^4$ is methyl.

9. A compound according to claim 1 wherein $R^6$ is

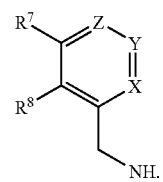

10. A compound according to claim 1 wherein Y is N.

11. A compound according to claim 10 wherein X is CH, Z is C-Me and $R^7$ is H and $R^8$ is Me.

12. A compound according to claim 10 wherein X is CH, Z is C-Me and $R^7$ and $R^8$ are both H.

13. A compound according to claim 10 wherein X is CH, Z is C-CF$_3$ and $R^7$ and $R^8$ are both H.

14. A compound according to claim 1 wherein X is N.

15. A compound according to claim 14 wherein Y is C-Me, Z is CH and $R^7$ and $R^8$ are both H.

16. A compound according to claim 14 wherein Y and Z are CH, $R^7$ is H and $R^8$ is Me.

17. A compound according to claim 1 wherein Z is N.

18. A compound according to claim 17 wherein X is CH, Y is C-Me, $R^7$ is Me and $R^8$ is H.

19. A compound according to claim 1 wherein $R^6$ is cyclopropylamino, cyclopropylmethylamino, cyclobutylamino, or cyclobutylmethylamino.

20. A compound according to claim 1 wherein $R^5$ is isopropyl.

21. A compound according to claim 1 which is selected from the following:

[1] (2R,3S-3-(6-((4,6-Dimethylpyridin-3-ylmethylamino)-9-isopropyl-9H-purin-2-ylamino)pentan-2-ol
[6] 2R,3S-3-(6-Cyclopropylamino)-9-isopropyl-9H-purin-2-ylamino)pentan-2-ol
[7] 2R,3S-3-(6-(Cyclopropylmethylamino)-9-isopropyl-9H-purine-2-ylamino)pentan-2-ol
[8] 2R,3S-3-(6-(Cyclobutylamino)-9-isopropyl-9H-purin-2-ylamino)pentan-2-ol
[10] 2R,3S-3-(9-Isopropyl-6-(2,6-dimethylpyridine-4-ylmethylamino)-9H-purin-2-ylamino)pentan-2-ol
[11] 2R,3S-3-(9-Isopropyl-6-((6-(trifluoromethyl)pyridine-3-yl)methylamino)-9H-purin-2ylamino)pentan-2-ol
[12] 2R,3S-3-(9-Isopropyl-6-((6-methylpyridin-2-yl)methylamino)-9H-purin-2-ylamino)pentan-2-ol
[13] 2R,3S-3-(9-Isopropyl-6-((3-methylpyridin-2-yl)methylamino)-9H-purin-2-ylamino)pentan-2-ol
[17] 1,1,1-Trifluoro-3-(9-isopropyl-6-((6-(trifluoromethyl)pyridin-3-yl)methylamino)-9H-2-ylamino)pentan-2-ol.

22. A compound of formula II, or a pharmaceutically acceptable salt thereof,

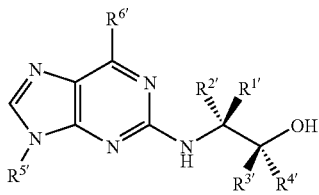

(II)

wherein:
- at least one of $R^{1'}$, $R^{2'}$, $R^{3'}$ and $R^{4'}$ is haloalkyl and the remainder are each independently H, alkyl or haloalkyl,;
- $R^{5'}$ is alkyl or cycloalkyl or cycloalkyl-alkyl, each of which may be optionally substituted with one or more OH groups;
- $R^{6'}$ is selected from cyclopropylamino, cyclopropylmethylamino, cyclobutylamino, cyclobutylmethylamino and

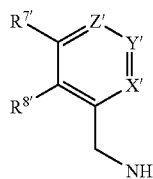

where X', Y' and Z' are each independently $CR^{9'}$, or one of X', Y' and Z' is N and the remainder are $CR^{9'}$; and $R^{7'}$, $R^{8'}$ and each $R^{9'}$ are independently H, halo, alkyl or haloalkyl.

23. A compound according to claim 22 wherein $R^{5'}$ is isopropyl.

24. A compound according to claim 22 wherein $R^{6'}$ is

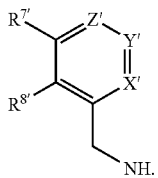

25. A compound according to claim 22 wherein Y' is N, X' and Z' are CH, and $R^{7'}$ and $R^{8'}$ are both H.

26. A compound according to claim 22 wherein one of $R^{1'}$ and $R^{2'}$ is H and the other is alkyl, or $R^{1'}$ and $R^{2'}$ are both H.

27. A compound according to claim 22 wherein one of $R^{3'}$ and $R^{4'}$ is H and the other is $CF_3$.

28. A compound according to claim 22 which is selected from the following:

[16] 1,1,1-Trifluoro-3-(9-isopropyl-6-(pyridin-3-ylmethylamino)-9H-purin-2-ylamino)pentan-2-ol
[18] 1,1,1,3,3,3-Hexafluoro-2-((9-isopropyl-6-(pyridine-3-ylmethylamino)-9H-purin-2-ylamino)methyl)propan-2-ol.

29. A compound selected from the following:

[1] (2R,3S-3-(6-((4,6-Dimethylpyridin-3-ylmethylamino)-9-isopropyl-9H-purin-2-ylamino)pentan-2-ol
[3] 2R,3S-3-(6-(3-Chlorobenzylamino)-9-isopropyl-9H-purin-2-ylamino)pentan-2-
[4] 2R,3S-3-[6-(3-Fluorobenzylamino)-9-isopropyl-9H-purin-2-ylamino]-pentan-2-ol
[6] 2R,3S-3-(6-Cyclopropylamino)-9-isopropyl-9H-purin-2-ylamino)pentan-2-ol
[7] 2R,3S-3-(6-(Cyclopropylmethylamino)-9-isopropyl-9H-purine-2-ylamino)pentan-2-ol
[8] 2R,3S-3-(6-(Cyclobutylamino)-9-isopropyl-9H-purin-2-ylamino)pentan-2-ol
[10] 2R,3S-3-(9-Isopropyl-6-(2,6-dimethylpyridine-4-ylmethylamino)-9H-purin-2-ylamino)pentan-2-ol
[11] 2R,3S-3-(9-Isopropyl-6-((6-(trifluoromethyl)pyridine-3-yl)methylamino)-9H-purin-2ylamino)pentan-2-ol
[12] 2R,3S-3-(9-Isopropyl-6-((6-methylpyridin-2-yl)methylamino)-9H-purin-2-ylamino)pentan-2-ol
[16] 1,1,1-Trifluoro-3-(9-isopropyl-6-(pyridin-3-ylmethylamino)-9H-purin-2-ylamino)pentan-2-ol
[17] 1,1,1-Trifluoro-3-(9-isopropyl-6-((6-(trifluoromethyl)pyridin-3-yl)methylamino)-9H-2-ylamino)pentan-2-ol
[18] 1,1,1,3,3,3-Hexafluoro-2-((9-isopropyl-6-(pyridine-3-ylmethylamino)-9H-purin-2-ylamino)methyl)propan-2-ol.

30. A compound according to claim 29 selected from the following:

[1] (2R,3S-3-(6-((4,6-Dimethylpyridin-3-ylmethylamino)-9-isopropyl-9H-purin-2-ylamino)pentan-2-ol
[3] 2R,3S-3-(6-(3-Chlorobenzylamino)-9-isopropyl-9H-purin-2-ylamino)pentan-2-
[4] 2R,3S-3-[6-(3-Fluorobenzylamino)-9-isopropyl-9H-purin-2-ylamino]-pentan-2-ol
[6] 2R,3S-3-(6-Cyclopropylamino)-9-isopropyl-9H-purin-2-ylamino)pentan-2-ol
[7] 2R,3S-3-(6-(Cyclopropylmethylamino)-9-isopropyl-9H-purine-2-ylamino)pentan-2-ol
[8] 2R,3S-3-(6-(Cyclobutylamino)-9-isopropyl-9H-purin-2-ylamino)pentan-2-ol
[10] 2R,3S-3-(9-Isopropyl-6-(2,6-dimethylpyridine-4-ylmethylamino)-9H-purin-2-ylamino)pentan-2-ol
[11] 2R,3S-3-(9-Isopropyl-6-((6-(trifluoromethyl)pyridine-3-yl)methylamino)-9H-purin-2ylamino)pentan-2-ol.

31. The compound according to claim 29: (2R,3S-3-(6-((4,6-Dimethylpyridin-3-ylmethylamino)-9-isopropyl-9H-purin-2-ylamino)pentan-2-ol, or pharmaceutically acceptable salt or ester thereof.

32. A pharmaceutical composition comprising a compound according to claim 1 admixed with a pharmaceutically acceptable diluent, excipient or carrier, or a mixture thereof.

* * * * *

UNITED STATES PATENT AND TRADEMARK OFFICE
CERTIFICATE OF CORRECTION

PATENT NO. : 8,592,581 B2  
APPLICATION NO. : 12/573337  
DATED : November 26, 2013  
INVENTOR(S) : Peter William Sheldrake et al.

Page 1 of 1

It is certified that error appears in the above-identified patent and that said Letters Patent is hereby corrected as shown below:

On the title page in the Foreign Application Priority Data add the following information:

(30)    Foreign Application Priority Data

Apr. 4, 2007  (GB) ........................... 0706632.7

Signed and Sealed this
Eighteenth Day of March, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,592,581 B2 | Page 1 of 1 |
| APPLICATION NO. | : 12/573337 | |
| DATED | : November 26, 2013 | |
| INVENTOR(S) | : Sheldrake et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this
Fourteenth Day of April, 2015

Michelle K. Lee
*Director of the United States Patent and Trademark Office*